United States Patent
Berzinis et al.

(10) Patent No.: US 10,252,220 B2
(45) Date of Patent: *Apr. 9, 2019

(54) POROUS ASYMMETRIC POLYPHENYLENE ETHER MEMBRANES AND ASSOCIATED SEPARATION MODULES AND METHODS

(71) Applicant: SABIC GLOBAL TECHNOLOGIES B.V., Bergen op Zoom (NL)

(72) Inventors: Albin Peter Berzinis, Delmar, NY (US); Pooja Bajaj, Schenectady, NY (US); Rachel Elizabeth Halbfinger, Glenville, NY (US); Matias Bikel, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 112 days.

This patent is subject to a terminal disclaimer.

(21) Appl. No.: 15/302,276

(22) PCT Filed: Apr. 30, 2015

(86) PCT No.: PCT/US2015/028546
§ 371 (c)(1),
(2) Date: Oct. 6, 2016

(87) PCT Pub. No.: WO2015/168423
PCT Pub. Date: Nov. 5, 2015

(65) Prior Publication Data
US 2017/0056835 A1    Mar. 2, 2017

Related U.S. Application Data

(60) Provisional application No. 61/987,389, filed on May 1, 2014.

(51) Int. Cl.
*A61M 1/16* (2006.01)
*C02F 1/44* (2006.01)
(Continued)

(52) U.S. Cl.
CPC ........... *B01D 69/02* (2013.01); *A61M 1/1621* (2014.02); *B01D 61/14* (2013.01); *B01D 61/145* (2013.01);
(Continued)

(58) Field of Classification Search
None
See application file for complete search history.

(56) References Cited

U.S. PATENT DOCUMENTS

| 3,446,856 A | 3/1969 | Hamilton |
| 3,522,326 A | 7/1970 | Bostick et al. |

(Continued)

FOREIGN PATENT DOCUMENTS

| CN | 103007787 A | 4/2013 |
| CN | 103170259 B | 12/2014 |

(Continued)

OTHER PUBLICATIONS

Machine Translation for JPH011322921A.
(Continued)

*Primary Examiner* — Krishnan S Menon
(74) *Attorney, Agent, or Firm* — Cantor Colburn LLP

(57) ABSTRACT

A porous asymmetric membrane comprises a hydrophobic polymer comprising a poly(phenylene ether) or poly(phenylene ether) copolymer; and a polymer additive. A separation module can be fabricated from the porous asymmetric membrane. A method of forming the porous asymmetric membrane comprises: dissolving a hydrophobic polymer comprising a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric
(Continued)

membrane. The polymer additive comprises hydrophilic functional groups, copolymerized hydrophilic monomers, or blocks of hydrophilic monomer repeat units. For example, the polymer additive can comprise a hydrophilic polymer or amphiphilic polymer. The porous asymmetric membrane can be a flat membrane or hollow fiber.

19 Claims, 4 Drawing Sheets

(51) Int. Cl.
| | |
|---|---|
| C07K 1/34 | (2006.01) |
| B01D 61/14 | (2006.01) |
| B01D 61/36 | (2006.01) |
| B01D 63/02 | (2006.01) |
| B01D 67/00 | (2006.01) |
| B01D 69/02 | (2006.01) |
| B01D 69/06 | (2006.01) |
| B01D 69/08 | (2006.01) |
| B01D 69/12 | (2006.01) |
| B01D 71/28 | (2006.01) |
| B01D 71/52 | (2006.01) |
| B01D 71/56 | (2006.01) |
| B01D 71/76 | (2006.01) |
| B01D 71/78 | (2006.01) |
| B01D 71/80 | (2006.01) |
| C08B 37/00 | (2006.01) |
| C02F 101/32 | (2006.01) |

(52) U.S. Cl.
CPC ........... *B01D 61/364* (2013.01); *B01D 63/02* (2013.01); *B01D 67/0016* (2013.01); *B01D 67/0095* (2013.01); *B01D 69/06* (2013.01); *B01D 69/08* (2013.01); *B01D 69/088* (2013.01); *B01D 69/125* (2013.01); *B01D 71/28* (2013.01); *B01D 71/52* (2013.01); *B01D 71/56* (2013.01); *B01D 71/76* (2013.01); *B01D 71/78* (2013.01); *B01D 71/80* (2013.01); *C02F 1/441* (2013.01); *C07K 1/34* (2013.01); *C08B 37/0003* (2013.01); *B01D 2323/02* (2013.01); *B01D 2323/04* (2013.01); *B01D 2323/22* (2013.01); *B01D 2323/36* (2013.01); *B01D 2323/40* (2013.01); *B01D 2325/022* (2013.01); *B01D 2325/34* (2013.01); *B01D 2325/36* (2013.01); *B01D 2325/38* (2013.01); *C02F 2101/32* (2013.01); *Y02W 10/37* (2015.05)

(56) References Cited

U.S. PATENT DOCUMENTS

| | | |
|---|---|---|
| 3,703,564 A | 11/1972 | White |
| 3,770,699 A | 11/1973 | White |
| 3,970,640 A | 7/1976 | Yonemitsu et al. |
| 4,201,880 A | 5/1980 | Van Sorge |
| 4,277,344 A | 7/1981 | Cadotte |
| 4,278,777 A | 7/1981 | Jakabhazy et al. |
| 4,338,421 A | 7/1982 | Maruyama et al. |
| 4,454,284 A | 6/1984 | Ueno et al. |
| 4,622,206 A | 11/1986 | Torgeson |
| 4,882,168 A | 11/1989 | Casey et al. |
| 4,933,081 A | 6/1990 | Sasaki et al. |
| 4,944,775 A | 7/1990 | Hayes |
| 5,069,793 A | 12/1991 | Kaschemekat et al. |
| 5,118,327 A | 6/1992 | Nelson et al. |
| 5,128,421 A | 7/1992 | Ohmura et al. |
| 5,132,363 A | 7/1992 | Furuta et al. |
| 5,159,027 A | 10/1992 | Kanayama et al. |
| 5,209,849 A | 5/1993 | Hu et al. |
| 5,282,964 A | 2/1994 | Young et al. |
| 5,385,976 A | 1/1995 | Furuta et al. |
| 5,480,552 A | 1/1996 | Soltys et al. |
| 5,527,467 A | 6/1996 | Oftshun et al. |
| 5,643,968 A | 7/1997 | Andreola et al. |
| 5,795,920 A | 8/1998 | Kang et al. |
| 5,834,583 A | 11/1998 | Hancock et al. |
| 6,294,499 B1 | 9/2001 | Watson et al. |
| 6,437,084 B1 | 8/2002 | Birsak et al. |
| 6,472,499 B1 | 10/2002 | Braat et al. |
| 7,166,148 B2 | 1/2007 | Lyons et al. |
| 7,208,438 B2 | 4/2007 | Ingelbrecht et al. |
| 8,222,342 B2 | 7/2012 | Weber et al. |
| 8,287,735 B2 | 10/2012 | Hanemaaijer et al. |
| 8,302,781 B2 | 11/2012 | Wechs et al. |
| 8,505,745 B2 | 8/2013 | Mayes et al. |
| 8,602,221 B2 | 12/2013 | Mizomoto et al. |
| 8,727,136 B2 | 5/2014 | Ansorge et al. |
| 8,741,600 B2 | 6/2014 | Yamaguchi et al. |
| 9,133,338 B2 | 9/2015 | Yang et al. |
| 2004/0145127 A1 | 7/2004 | Pinto |
| 2004/0149127 A1 | 8/2004 | Lyons et al. |
| 2004/0231663 A1 | 11/2004 | Carter et al. |
| 2005/0218057 A1 | 10/2005 | Ngee |
| 2006/0076884 A1 | 4/2006 | Ahn |
| 2006/0076885 A1 | 4/2006 | Kim et al. |
| 2006/0137522 A1 | 6/2006 | Nishimura et al. |
| 2007/0068871 A1 | 3/2007 | Flynn |
| 2007/0202374 A1 | 8/2007 | Bridges et al. |
| 2007/0238832 A1 | 10/2007 | Borade et al. |
| 2008/0076884 A1 | 3/2008 | Yeager et al. |
| 2008/0076885 A1 | 3/2008 | Yeager et al. |
| 2008/0085989 A1 | 4/2008 | Yeager et al. |
| 2008/0142429 A1 | 6/2008 | Zhang et al. |
| 2008/0203012 A1 | 8/2008 | Yeager et al. |
| 2008/0207822 A1 | 8/2008 | Yeager et al. |
| 2008/0312349 A1 | 12/2008 | Yeager et al. |
| 2009/0018303 A1 | 1/2009 | Onizuka et al. |
| 2010/0244306 A1 | 9/2010 | Tang |
| 2012/0100904 A1 | 5/2012 | Morita et al. |
| 2012/0103904 A1 | 5/2012 | Morita et al. |
| 2012/0277347 A1 | 11/2012 | Bedner et al. |
| 2012/0305486 A1 | 12/2012 | Storr et al. |
| 2013/0220924 A1 | 8/2013 | Maeda |
| 2016/0008528 A1 | 1/2016 | Roy et al. |
| 2016/0021191 A1 | 1/2016 | Wang et al. |
| 2016/0022892 A1 | 1/2016 | Eifler et al. |
| 2016/0079616 A1 | 3/2016 | Lee et al. |
| 2017/0282131 A1 | 10/2017 | Berzinis et al. |
| 2018/0079863 A1 | 3/2018 | Ghanta |

FOREIGN PATENT DOCUMENTS

| | | |
|---|---|---|
| EP | 0216633 | 4/1987 |
| EP | 0568045 A1 | 11/1993 |
| EP | 0083489 B1 | 4/1999 |
| EP | 1918019 A1 | 5/2008 |
| EP | 2535101 A1 | 12/2012 |
| JP | S42004276 B | 2/1964 |
| JP | S46002837 B | 10/1967 |
| JP | S46006542 | 12/1971 |
| JP | S60114323 A | 6/1985 |
| JP | S62057915 | 3/1987 |
| JP | S62071503 A | 4/1987 |
| JP | S62152507 A | 7/1987 |
| JP | S63100916 A | 5/1988 |
| JP | S63128021 A | 5/1988 |
| JP | S63197502 | 8/1988 |
| JP | S63218231 A | 9/1988 |
| JP | S63230173 A | 9/1988 |
| JP | H03065227 A | 3/1991 |
| JP | H04011927 | 1/1992 |
| JP | H08143699 A | 6/1996 |
| JP | S64030621 | 2/1999 |
| JP | H11156165 A | 6/1999 |
| JP | H11322921 A | 11/1999 |
| JP | 2000246064 A | 9/2000 |
| JP | 2004231743 A | 8/2004 |

(56) References Cited

FOREIGN PATENT DOCUMENTS

| | | |
|---|---|---|
| JP | 2005262211 A | 9/2005 |
| JP | 2013013838 A | 1/2013 |
| JP | 2014205761 A | 10/2014 |
| WO | 0240140 A1 | 5/2002 |
| WO | 03000389 A2 | 1/2003 |
| WO | 2004056459 A1 | 7/2004 |
| WO | 2005107929 A2 | 11/2005 |
| WO | 2008036454 | 3/2008 |
| WO | 2008103599 A2 | 8/2008 |
| WO | 2012008837 A2 | 1/2012 |
| WO | 2013131848 A1 | 9/2013 |
| WO | 2014195234 A1 | 12/2014 |
| WO | 2015168392 A1 | 11/2015 |
| WO | 2015168409 A1 | 11/2015 |
| WO | 2015168414 A1 | 11/2015 |
| WO | 2015168584 A1 | 11/2015 |
| WO | 2015168592 A1 | 11/2015 |
| WO | 2015168418 A1 | 11/2016 |
| WO | 2016178835 A1 | 11/2016 |

OTHER PUBLICATIONS

Advisory Action dated Aug. 8, 2017 for U.S. Appl. No. 15/356,836; 4 Pages.
International Preliminary Report on Patentability for International Application No. PCT/US2016/028951; Date of Filing: Apr. 22, 2016; dated Aug. 7, 2017; 57 pages.
Machine Translation for JPH08143699.
Machine Translation for JPS46006542.
Machine Translation for JPS62152507A.
Non-Final Office Action dated Jan. 4, 2018 for U.S. Appl. No. 15/536,836; 11 Pages.
U.S. Notice of Allowance, U.S. Appl. No. 15/356,854, dated Aug. 16, 2017, 16 pages.
Written Opnion of the International Searching Authority for International Application No. PCT/US2016/028951; Date of Filing: Apr. 22, 2016; dated Apr. 11, 2017; 10 pages.
Final Office Action for U.S. Appl. No. 15/356,836 dated Apr. 20, 2018, 22 pages.
Machine Translation for JPH08143699 obtained from Espacenet on Jan. 12, 2018, 10 pages; (https://worldwide.espacenet.com/publicationDetails/biblio?II=0&ND=3&adjacent=true&locale=en_EP&FT=D&date=19960604&CC=JP&NR=H08143699A&KC=A#).
Machine Translation for JPS4665420A obtained from J-Plat Pat on Jan. 8, 2018, 14 pages; (https://www4.j-platpat.inpit.go.jp/cgi-bin/tran_web_cgi_ejje?u=http://www4.j-platpat.inpit.go.jp/eng/translation/201804240506474023768556212174105
6C2CF07F06D8BF80DAC7BA11D51D95A0).
Machine Translation for JPS62152507A obtained from Espacenet on Jan. 12, 2018, 11 pages; (https://worldwide.espacenet.com/publicationDetails/biblio?II=0&ND=3&adjacent=true&locale=en_EP&FT=D&date=19870707&CC=JP&NR=S62152507A&KC=A#).
Non-Final Office Action for U.S. Appl. No. 15/303;562; dated Feb. 6, 2016.
Non-Final Office Action for U.S. Appl. No. 15/303,556; dated May 3, 2018; 30 pages.
Restriction Requirement for U.S. Appl. No. 15/302,323 dated Apr. 30, 2018; 8 pages.
Restriction Requirement for U.S. Appl. No. 15/303,058; dated May 1, 2018; 8 pages.
Restriction Requirement for U.S. Appl. No. 15/303,061; dated May 4, 2018; 8 pages.
Restriction Requirement for U.S. Appl. No. 15/303,561; dated Apr. 27, 2018; 10 pages.
Asatekin et al.; "Anti-fouling ultrafiltration membranes containing polyacrylonitrile-graft-poly(ethylene oxide) comb copolymer additives"; Journal of Membrane Science 298 (2007) pp. 136-146.
ATRP Solutions; 2011 Catalog; 9 pages.
Baker; "Membranes and Modules"; Membrane Technology & Applications, Third Edition; 2012 John Wiley & Sons; pp. 97-178.
Bernardo et al.; "Membrane Gas Separation: A Review/State of the Art"; Ind. Eng. Chem. Res. 2009, 48, pp. 4638-4663.
Chung et al.; "Formation of ultrathin high-performance polyethersulfone hollow-fiber membranes"; Journal of Membrane Science 133 (1997) pp. 161-175.
Cooper et al.; "Preparation and Properties of Poly(arylene oxide) Copolymers"; Advances in Chemistry; American Chemical Society; 1973; pp. 230-257.
Cooper et al.; "Preparation and Properties of Polyarylene Oxide Copolymers"; 1973; pp. 551-556.
Dongliang et al.; "Polyethersulfone hollow fiber gas separation membranes prepared from NMP/alcohol solvent systems"; Journal of Membrane Science; 115; 1996, pp. 85-108.
International Search Report for International Application No. PCT/US2015/028546, International Filing Date Apr. 30, 2015, dated Aug. 4, 2015, 5 pages.
International Search Report for International Application No. PCT/US2015/028831, International Filing Date May 1, 2015, dated Jul. 30, 2015, 5 pages.
Kang et al.; "Protein antifouling mechanisms of PAN UF membranes incorporating PAN-g-PEO additive"; Journal of Membrane Science 296 (2007) pp. 42-50.
Kim et al.; "Ultrafiltration membranes prepared from blends of polyethersulfone and poly(1-vinylpyrrolidone-co-styrene) copolymers"; Journal of Membrane Science 262 (2005) pp. 60-68.
Liang et al.; "Synthesis and characterization of poly(phenylene oxide) graft copolymers by atom transfer radical polymerizations"; European Polymer Journal 45 (2009) pp. 2348-2357.
Petersen; "Composite reverse osmosis and nanofiltration membranes"; Journal of Membrane Science, 83 (1993) pp. 81-150.
Semsarzadeh et al.; "Synthesis and Characterization of Poly(phenylene oxide)-Based Block Copolymers via Cobalt Radical Mediated Polymerization (CMRP)"; Silicon; 6, 2014, pp. 27-34.
Smid et al.; "The formation of asymmetric hollow fibre membranes for gas separation, using PPE of different intrinsic viscosities"; Journal of Membrane Science, 64, 1991, pp. 121-128.
Ulbricht, "Advanced functional polymer membranes", Polymer; 47; Jan. 2006; pp. 2217-2262.
Vandezande et al.; "High throughput study of phase inversion parameters for polyimide-based SRNF membranes"; Journal of Membrane Science, 330, 2009, pp. 307-318.
Wang et al.; "Highly permeable polyethersulfone hollow fiber gas separation membranes prepared using water as non-solvent additive"; Journal of Membrane Science 176 (2000) pp. 147-158.
Wang et al.; "Polyethersulfone hollow fiber gas separation membranes prepared from NMP/alcohol solvent systems"; Journal of Membrane Science 115 (1996) pp. 85-108.
Written Opinion for International Application No. PCT/US2015/028546, International Filing Date Apr. 30, 2015, dated Aug. 4, 2015.
Written Opinion for International Application No. PCT/US2015/028831, International Filing Date May 1, 2015, dated Jul. 30, 2015, 8 pages.
Yang et al.; "Tailoring pore size and pore size distribution of kidney dialysis hollow fiber membranes via dual-bath cpagulation approach"; Journal of Membrane Science 290 (2007) pp. 153-163.
Yeager et al.; "Polyethers, Aromatic"; Encyclopedia of Polymer Science and Technology; vol. 11; John Wiley & Sons; 2003; pp. 64-87.
Non Final Office Action for U.S. Appl. No. 15/303,561; dated Jul. 26, 2018; 16 pages.
Advisory Action for U.S. Appl. No. 15/356,836, dated Jul. 3, 2018; 9 Pages.
Li et al., Ed., "Water Treatment and Water Quality Control of Power Station"; China Electric Power Press; 2012; pp. 203-204.
Li et al., Ed., "Water Treatment and Water Quality Control of Power Station"; China Electric Power Press; 2012; pp. 203-204 (Original in Chinese).
Non Final Office Action for U.S. Appl. No. 15/303,061; dated Jul. 19, 2018; 53 pages.
Non-Final Office Action for U.S. Appl. No. 15/302,323; dated Jul. 19, 2018; 51 pages.

(56) References Cited

OTHER PUBLICATIONS

Non-Final Office Action for U.S. Appl. No. 15/303,058; dated Jul. 19, 2018; 56 pages.
Notice of Allowance for U.S. Appl. No. 15/303,562; dated Jun. 1, 2018; 25 pages.
Shi et al., Ed., "Membrane Technology Manual"; Chemical industry Press; 2001; p. 199 (Original in Chinese).
Shi et al., Ed., "Membrane Technology Manual"; Chemical industry Press; 2001; p. 199.
Wang, Ed. "Biomedical Engineering Principles"; Science Press; 1982; p. 326 (Original in Chinese).
Wang, Ed. "Biomedical Engineering Principles"; Science Press; 1982; p. 326.
Wang, Ed., "Membrane Separation Technology and Use Thereof"; Science Press; 1994; p. 181 (Original in Chinese).
Wang, Ed., "Membrane Separation Technology and Use Thereof"; Science Press; 1994; p. 181.
Zhong et al., Ed., "Principle of Chemical Industry"; National Defense Industry Press; 2013; p. 399 (Original in Chinese).
Zhong et al., Ed., "Principle of Chemical Industry"; National Defense Industry Press; 2013; p. 399.
CN 103170259; Machine Translation; Date of Publication: Dec. 10, 2014; 10 pages.
Final Office Action dated Jun. 7, 2017; U.S. Appl. No. 15/356,836, filed Nov. 21, 2016; 16 pages.
International Search Report for International Application No. PCT/US2016/028951; International Filing Date Apr. 2016; dated Jul. 29, 2016; 7 pages.
International Search Report for International Application No. PCT/US2017/022061; date of Filing: Mar. 13, 2017; dated Jul. 4, 2017; 6 pages.
International Search Report for International Application No. PCT/US2017/022088; Date of Filing: Mar. 13, 2017; dated Jun. 28, 2017; 6 pages.
JP S60114323; Machine Translation; Date of Publication: Jun. 20, 1985; 8 pages.
Loh et al.; "Fabrication of high performance polyethersulfone UF hollow fiber membranes using amphiphilic Pluronic block copolymers as pore-forming additives"; J. Membr. Sci., vol. 380; 2011; 114-123.
Non-Final Office Action dated Feb. 16, 2017; U.S. Appl. No. 15/356,836, filed Nov. 21, 2016; 24 pages.
Non-Final Office Action dated Mar. 6, 2017; U.S. Appl. No. 15/356,854, filed Nov. 21, 2016; 28 pages.
Susanto et al.; "Characteristics, performance and stability of polyethersulfone ultrafiltration membranes prepared by phase separation method using different macromolecular additives"; J. Membr. Sci., vol. 327; 2009; p. 125-135.
U.S. Appl. No. 15/356,836 to Berzinis; filed Nov. 21, 2016; 29 pages.
U.S. Appl. No. 15/356,854 to Berzinis; filed Nov. 21, 2016; 38 pages.
U.S. Appl. No. 62/155,593 to Berzinis; filed May 1, 2015; 36 pages.
Written Opinion of the International Search Report for International Application No. PCT/US2016/028951; International Filing Date Apr. 22, 2016; dated Jul. 29, 2016; 9 pages.
Written Opinion of the International Searching Authority for International Application No. PCT/US2017/022061; Date of Filing: Mar. 13, 2017; dated Jul. 4, 2017; 9 pages.
Written Opinion of the International Searching Authority for International Application No. PCT/US2017/022088; Date of Filing: Mar. 13, 2017; dated Jun. 28, 2017; 8 pages.

SEM OF MEMBRANE SURFACES:

COMPARATIVE EXAMPLE 2
14% 6020P / 5% K30 / 2%
K90 / 3% H2O IN NMP

EXAMPLE 17
50/50 MPP/DMP
18% IN NMP

SEM OF MEMBRANE CROSS-SECTIONS:

COMPARATIVE EXAMPLE 2

EXAMPLE 17

COMPARATIVE EXAMPLE 3
FIBER SPUN FROM DOPE SOLUTION
OF 14% 6020P / 5% K30 / 2% K90 /
3% H2O / 76% NMP

EXAMPLE 18
FIBER SPUN FROM DOPE SOLUTION
OF 18% EX. 12 / 82% NMP

POROUS ASYMMETRIC POLYPHENYLENE ETHER MEMBRANES AND ASSOCIATED SEPARATION MODULES AND METHODS

CROSS REFERENCE TO RELATED APPLICATIONS

This application is a National Stage application of PCT/US2015/028546, filed Apr. 30, 2015, which claims the benefit of U.S. Provisional Application No. 61/987,389, filed May 1, 2014, both of which are incorporated by reference in their entirety herein.

BACKGROUND OF THE INVENTION

Reverse osmosis is utilized in membrane separation process whereby a feed stock containing a solute, which has molecular or colloidal dimensions which are significantly greater than the molecular dimensions of its solvent, is depleted of the solute by being contacted with the membrane at such pressure that the solvent permeates the membrane and the solute is retained. This results in a permeate fraction which is solute-depleted and a retentate fraction which is solute-enriched. In ultrafiltration, microfiltration, ultrafiltration, and nanofiltration, pressure in excess of the osmotic pressure can be used to force the solvent through the membrane against a concentration gradient of solute.

Poly(phenylene ether)s are a class of plastics having excellent water resistance, thermal resistance, and dimensional stability. They retain their mechanical strength in hot, and/or wet environments. Therefore they can be used for the fabrication of porous asymmetric membranes useful in various separation processes, including reverse osmosis. For example, poly(phenylene ether)s can be used in processes that require repeated cleaning with hot water or steam sterilization. Nonetheless, there remains a need for a porous asymmetric membrane having improved filtration properties, including materials that will improve selectivity without adversely affecting permeation flux.

The surface of membranes fabricated from hydrophobic polymers can be made hydrophilic by blending with a polymer additive that is hydrophilic. For example, polyethersulfone can be blended with poly(N-vinylpyrrolidone), and the two polymers can be co-precipitated from solution to form a membrane. However, excess poly(N-vinylpyrrolidone) must be washed off of the membrane with water, which results in a waste of valuable material, and which produces an aqueous waste comprising the excess poly(N-vinylpyrrolidone). Moreover the hydrophilic polymer can be leached out of the membrane in membrane treatment of aqueous streams. There remains a need for a polymer additive that provides a hydrophilic surface to porous asymmetric membranes fabricated from hydrophobic polymers. The polymer additive should have hydrophilic character and yet have an affinity for the hydrophobic polymer, so that the polymer additive is not extracted by washing during fabrication or in end-use operation of the membrane.

BRIEF DESCRIPTION OF THE INVENTION

A porous asymmetric membrane comprises, consists essentially of, or consists of a hydrophobic polymer comprising, consisting essentially of, or consisting of a poly(phenylene ether) or poly(phenylene ether) copolymer; and a polymer additive. A separation module can be fabricated from the porous asymmetric membrane.

A method of forming the porous asymmetric membrane comprises: dissolving a hydrophobic polymer comprising, consisting essentially of, or consisting of a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric membrane.

A method of making a hollow fiber by coextrusion through a spinneret comprising an annulus and a bore, comprises coextruding: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber. A hollow fiber made by the method can be fabricated into a separation module.

BRIEF DESCRIPTION OF THE DRAWINGS

Referring now to the drawings.

DETAILED DESCRIPTION OF THE INVENTION

Figure 1:
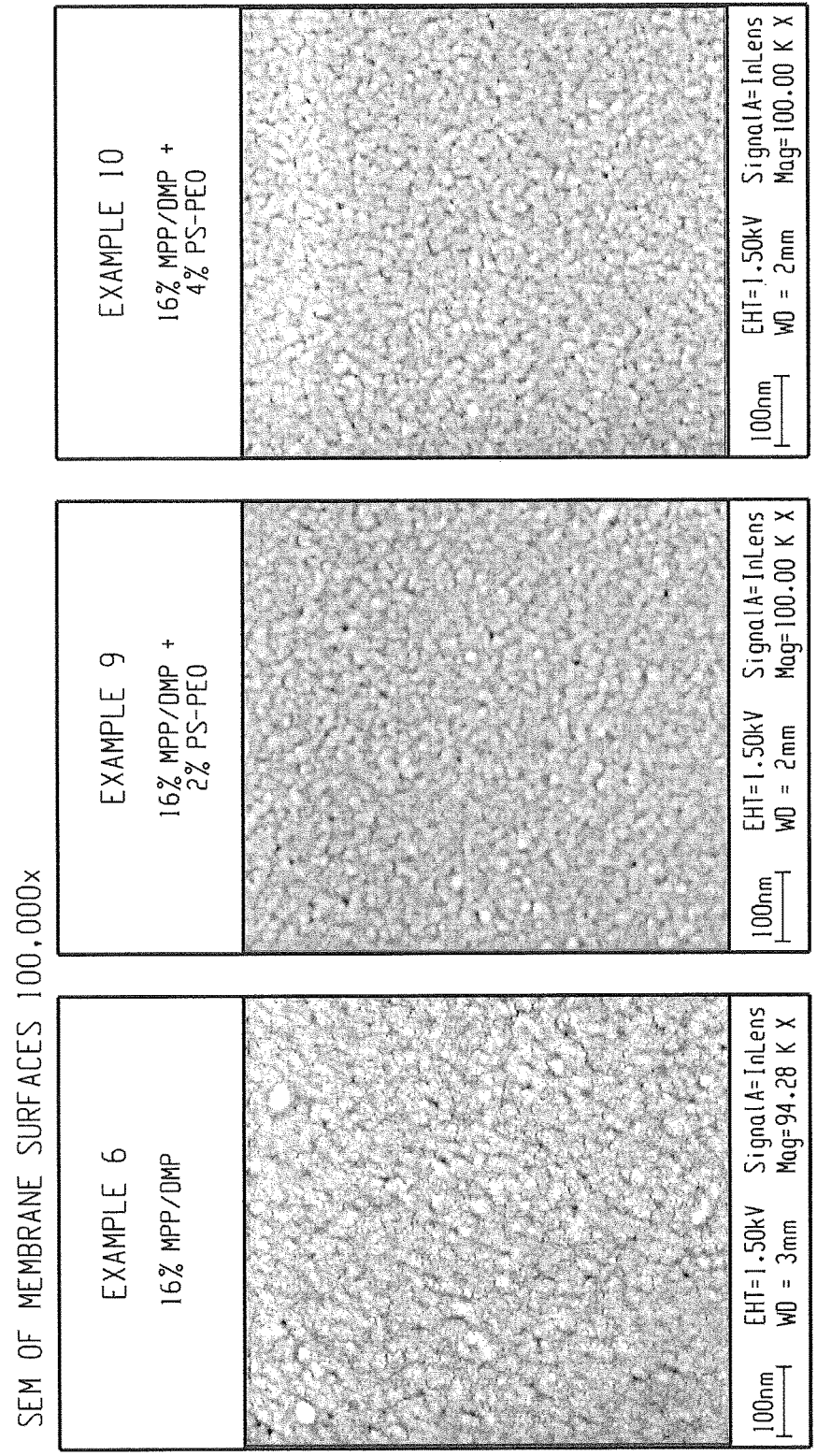
FIG. 1 depicts scanning electron microscopy (SEM) images of the porous asymmetric membrane surfaces Examples 6 and 9-10.

The inventors hereof have discovered specific polymer additives that are particularly effective in combination with hydrophobic polymers comprising poly(phenylene ether) or poly(phenylene ether) copolymer; for the manufacture of asymmetric membranes and hollow fibers used in ultrafiltration. The polymer additive can comprise hydrophilic functional groups, copolymerized hydrophilic monomers, or blocks of hydrophilic monomer repeat units. For example, the polymer additive can comprise a hydrophilic polymer or amphiphilic polymer. An amphiphilic polymer is a polymer that has both hydrophilic (water-loving, polar) and hydrophobic (water-hating, non-polar) properties.

Advantageously, use of the polymer additive in combination with a hydrophobic polymer comprising a poly(phenylene ether) or poly(phenylene ether) copolymer provides a porous asymmetric membranes having surface pore size distributions, surface pore densities, and water contact angles that make the porous asymmetric membrane suitable for use in separation modules for purification of aqueous streams by ultrafiltration. The polymer additive provides a more hydrophilic surface to porous asymmetric membranes fabricated from hydrophobic polymers comprising a poly (phenylene ether) or poly(phenylene ether) copolymer, and yet has an affinity for the poly(phenylene ether) or poly (phenylene ether) copolymer, so that it is not extracted by washing during fabrication or in end-use operation of the porous asymmetric membrane in separation modules.

The porous asymmetric membrane comprises consists essentially of, or consists of: a hydrophobic polymer comprising, consisting essentially of, or consisting of a poly (phenylene ether) or poly(phenylene ether) copolymer; and a polymer additive. In some embodiments, the hydrophobic polymer comprises a poly(phenylene ether) copolymer comprising first and second repeat units having the structure:

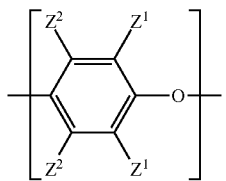

wherein each occurrence of $Z^1$ is independently halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy, wherein at least two carbon atoms separate the halogen and oxygen atoms; wherein each occurrence of $Z^2$ is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy, wherein at least two carbon atoms separate the halogen and oxygen atoms; and wherein the first and second repeat units are different.

In some embodiments, the hydrophobic polymer comprises a poly(phenylene ether) copolymer comprising, consisting essentially of, or consisting of: 80 to 20 mole percent repeat units derived from 2,6-dimethylphenol; and 20 to 80 mole percent repeat units derived from a first monohydric phenol having the structure

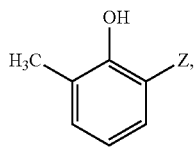

wherein Z is $C_1$-$C_{12}$ alkyl or cycloalkyl, or a monovalent radical having the structure

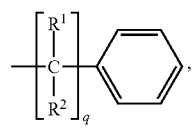

wherein q is 0 or 1, and $R^1$ and $R^2$ are independently hydrogen or $C_1$-$C_6$ alkyl; wherein the poly(phenylene ether) copolymer has an intrinsic viscosity of 0.7 to 1.5 deciliters per gram, measured in chloroform at 25° C. The first monohydric phenol can comprise 2-methyl-6-phenylphenol, and the hydrophobic polymer can comprise a copolymer having 20 to 80 mole percent of repeat units derived from 2-methyl-6-phenylphenol and 80 to 20 mole percent repeat units derived from 2,6-dimethylphenol. The copolymer can also be a copolymer of 2,6-dimethylphenol and 2,3,6-trimethylphenol, or a terpolymer of 2,6-dimethylphenol and 2,6-trimethylphenol, and 2,3,6-trimethylphenol.

The hydrophobic polymer can be a poly(phenylene ether) copolymer having an intrinsic viscosity greater than or equal to 0.7, 0.8, 0.9, 1.0, or 1.1 deciliters per gram, and less than or equal to 1.5, 1.4, or 1.3 deciliters per gram, when measured in chloroform at 25° C. In some embodiments, the intrinsic viscosity is 1.1 to 1.3 deciliters per gram.

In some embodiments, the poly(phenylene ether) copolymer has a weight average molecular weight of 100,000 to 500,000 daltons (Da), as measured by gel permeation chromatography against polystyrene standards. Within this range, the weight average molecular weight can be greater than or equal to 150,000 or 200,000 Da and less than or equal to 400,000, 350,000, or 300,000 Da. In some embodiments, the weight average molecular weight is 100,000 to 400,000 Da, specifically 200,000 to 300,000 Da. The poly (phenylene ether) copolymer can have a polydispersity (ratio of weight average molecular weight to number average molecular weight of 3 to 12. Within this range, the polydispersity can be greater than or equal to 4 or 5 and less than or equal to 10, 9, or 8.

The solubility of the hydrophobic polymer in water-miscible polar aprotic solvents can be 50 to 400 grams per kilogram at 25° C., based on the combined weight of the hydrophobic polymer and the solvent. Within this range, the solubility can be greater than or equal to 100, 120, 140, or 160 grams per kilogram, and less than or equal to 300, 250, 200, or 180 grams per kilogram at 25° C. Advantageously, the use hydrophobic polymers having an intrinsic viscosity of 0.7 to 1.5 deciliters per gram, specifically 1.1 to 1.3 deciliters per gram, and a solubility of 50 to 400 grams per kilogram at 25° C. results in membrane-forming compositions with solution concentrations and viscosities that provide good control over the phase inversion step of membrane formation.

The polymer additive can comprise hydrophilic functional groups, copolymerized hydrophilic monomers, or blocks of hydrophilic monomer repeat units. In some embodiments, the polymer additive comprises a hydrophilic polymer or an amphiphilic polymer. An amphiphilic polymer is defined herein as a polymer that has both hydrophilic (water-loving, polar) and hydrophobic (water-hating, nonpolar) properties. The amphiphilic polymer can be a random, alternating, periodic, graft, or block copolymer of hydrophilic and hydrophobic comonomers. The amphiphilic polymer can have star, comb, or brush branching. Thus, in some embodiments, the polymer additive comprises an amphiphilic block copolymer comprising a hydrophobic block and a hydrophilic block or graft. Amphiphilic block copolymers are differentiated from random copolymers of hydrophobic ethylenically unsaturated monomers and hydrophilic ethylenically unsaturated copolymers, for example a random copolymer of styrene and N-vinylpyrrolidone, in that the hydrophobic monomer repeat units and hydrophilic monomer repeat units are localized in homopolymer blocks comprising either comonomer. In some embodiments, the amphiphilic block copolymer comprises 20 to 50 weight percent of the hydrophobic block and 80 to 50 weight percent of the hydrophilic block or graft. In other embodiments, the amphiphilic block copolymer comprises 50 to 90 weight percent of the hydrophobic block and 50 to 10 weight percent of the hydrophilic block or graft.

The hydrophobic block of the amphiphilic block copolymer can comprise a polystyrene block and the hydrophilic block or graft of the amphiphilic block copolymer can comprise a polymerized ethylenically unsaturated monomer. The ethylenically unsaturated monomer can be selected from acrylic acid esters, methacrylic acid esters, hydroxyalkyl acrylates, hydroxyalkyl methacrylates, acrylamide derivatives, vinyl pyridines and alkyl-substituted derivatives thereof, vinyl carbazoles, vinyl acetate, vinyl sulfonic acid, vinyl phosphoric acid, 4-styrenesulfonic acid, N-vinylpyrrolidone, and combinations comprising at least one of the foregoing. Specific ethylenically unsaturated monomers comprise acrylic acid, methacrylic acid, ethyl methacrylate, ethyl acrylate, 2-hydroxyethyl acrylate, 2-hydroxypropyl acrylate, 3-hydroxypropyl acrylate, 1-hydroxy-prop-2-yl acrylate, 2-hydroxyprop-1-yl acrylate, 2,3-dihydroxypropyl acrylate, 2-hydroxyethyl methacrylate, maleic anhydride, acrylamide, N-methylacrylamide, N,N-dimethylacrylamide, vinyl acetate, 2-vinyl pyridine, 2-methyl-5-vinyl pyridine, 2-ethyl-5-vinyl pyridine, N-vinyl pyrrolidone, N-vinyl carbazole, vinyl sulfonic acid, vinyl phosphoric acid, phosphoethyl methacrylate, and combinations comprising at least one of the foregoing. In some embodiments, the ethylenically unsaturated monomer comprises methoxy-capped poly(ethylene oxide) methacrylate, 4-vinylpyridine, N-vinylpyrrolidone, N,N-dimethylacrylamide, 4-acryloylmorpholine, or a combination comprising at least one of the foregoing.

The amphiphilic block copolymer can be made by a method comprising polymerization of a hydrophilic ethylenically unsaturated monomer in the presence of a hydrophobic polymer comprising polystyrene, which includes oligomers thereof. The polymerization of the hydrophilic ethylenically unsaturated monomer can be controlled radical polymerization. In some embodiments, polymerization of the hydrophilic ethylenically unsaturated monomer is selected from atom transfer radical polymerization, reversible addition fragmentation transfer polymerization, and stable free radical polymerization. The polymerization of the hydrophilic ethylenically unsaturated monomer can be graft polymerization. In some embodiments, the hydrophilic ethylenically unsaturated monomer comprises methoxy capped poly(ethylene oxide) methacrylate, 4-vinylpyridine, vinyl pyrrolidone, N,N-dimethylacrylamide, 4-acryloylmorpholine, or a combination comprising at least one of the foregoing.

In some embodiments, the porous asymmetric membrane comprises a hydrophobic polymer comprising a poly(phenylene ether) or poly(phenylene ether) copolymer; and an amphiphilic block copolymer comprising a hydrophobic block and a hydrophilic block or graft wherein the hydrophobic block comprises a polystyrene block.

In some embodiments, the amphiphilic block copolymer comprises a hydrophobic block comprising polystyrene and a hydrophilic block or graft comprising poly(N,N-dimethylacrylamide) or poly(4-vinylpyridine). In some embodiments, the polymer additive comprises poly(vinyl pyrrolidone), poly(oxazoline), poly(ethylene glycol), poly(propylene glycol), a poly(ethylene glycol) monoether or monoester, a poly(propylene glycol) monoether or monoester, a block copolymer of poly(ethylene oxide) and poly(propylene oxide), polystyrene-graft-poly(ethylene glycol), polystyrene-graft-poly(propylene glycol), polysorbate, cellulose acetate, or a combination comprising at least one of the foregoing.

In some embodiments, the porous asymmetric membrane comprises a poly(phenylene ether) copolymer comprising 80 to 20 mole percent repeat units derived from 2,6-dimethylphenol; and 20 to 80 mole percent repeat units derived from 2-methyl-6-phenylphenol; and a polymer additive comprising poly(vinylpyrrolidone), poly(styrene-co-vinylpyrrolidone), polystyrene-block-poly(N,N-dimethylacrylamide) or a combination comprising as least one of the foregoing.

A method of forming the porous asymmetric membrane, comprises: dissolving a hydrophobic polymer comprising, consisting essentially of, or consisting of a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric membrane. All of the properties of the porous asymmetric membrane disclosed herein apply as well to the method of making the porous asymmetric membrane. For example, the method of forming the porous asymmetric membrane can comprise: dissolving a hydrophobic polymer comprising, consisting essentially of, or consisting of a poly(phenylene ether) copolymer comprising 80 to 20 mole percent repeat units derived from 2,6-dimethylphenol; and 20 to 80 mole percent repeat units derived from 2-methyl-6-phenylphenol; and a polymer additive comprising poly(vinylpyrrolidone), poly(styrene-co-vinylpyrrolidone), polystyrene-block-poly(N,N-dimethylacrylamide) or a combination comprising as least one of the foregoing, in N-methyl-2-pyrrolidone to form a porous asymmetric membrane-forming composition; and phase-inverting the porous asymmetric membrane forming-composition in a first non-solvent composition comprising water, N-Methyl-2-pyrrolidone, or a combination thereof, to form the porous asymmetric membrane.

In some embodiments, the method further comprises washing the porous asymmetric membrane in a second non-solvent composition. This step serves to rinse any residual water-miscible polar aprotic solvent from the membrane. The first and second non-solvent compositions can be the same or different, and can comprise water, or a mixture of water and a water-miscible polar aprotic solvent. In some embodiments the first and second non-solvents are independently selected from water, and a mixture of water and N-methyl-2-pyrrolidone mixture. In some embodiments, the first and second non-solvents are both water. The water can be deionized. In some embodiments, the method further comprises drying the membrane to remove residual first and second non-solvent composition, for example water and N-methyl-2-pyrrolidone.

The hydrophobic polymer is dissolved in a water-miscible polar aprotic solvent to form the membrane-forming composition. The water-miscible polar aprotic solvent can be, for example, N,N-dimethylformamide (DMF), N,N-dimethylacetamide (DMAC), N-methyl-2-pyrrolidone (NMP), N-ethyl-2-pyrrolidone, dimethyl sulfoxide (DMSO), dimethyl sulfone, sulfolane, butyrolactone; and combinations comprising at least one of the foregoing. In some embodiments, the water-miscible polar aprotic solvent is N-methyl-2-pyrrolidone. The solubility of the hydrophobic polymer in the water-miscible polar aprotic solvent can be 50 to 400 grams per kilogram at 25° C., based on the combined weight of the poly(phenylene ether) and the solvent. Within this range, the solubility can be greater than or equal to 100, 120, 140, or 160 grams per kilogram, and less than or equal to 300, 250, 200, or 180 grams per kilogram at 25° C. Advantageously, a hydrophobic solubility of 50 to 400 grams per kilogram provides membrane-forming compositions conducive to the formation of suitable porous membranes.

The first non-solvent composition comprises water, a water-miscible polar aprotic solvent, or a combination comprising at least one of the foregoing. The water-miscible polar aprotic solvent can be any of the water-miscible polar aprotic solvents used for the membrane-forming composition. In some embodiments, the first non-solvent composition comprises 10 to 100 weight percent water and 0 to 90 weight percent N-methyl-2-pyrrolidone, based on the total weight of the first non-solvent composition. Within this range, the first non-solvent composition can comprise 10 to 90 weight percent, specifically 10 to 80 weight percent, water and 10 to 90 weight percent, specifically 20 to 90 weight percent, N-methyl-2-pyrrolidone. In some embodiments, the first non-solvent composition comprises about 70 weight percent water and about 30 weight percent N-methyl-2-pyrrolidone. The first non-solvent composition serves as a coagulation, or phase inversion, bath for the membrane-forming composition. The membrane is formed by contacting the membrane-forming composition with the first non-solvent composition. The copolymer, which is near its gel point in the membrane-forming composition, coagulates, or precipitates as a film or hollow fiber.

The method includes phase-inverting the membrane-forming composition in the first non-solvent composition. Any of several techniques for phase inversion can be used. For example, the phase inversion can be a dry-phase separation method in which the dissolved copolymer is precipitated by evaporation of a sufficient amount of solvent mixture to form the membrane. The phase inversion step can also be a wet-phase separation method in which the dissolved copolymer is precipitated by immersion in the first non-solvent to form the membrane. The phase inversion step can be a dry-wet phase separation method, which is a combination of the dry-phase and the wet-phase methods. The phase inversion step can be a thermally-induced separation method in which the dissolved copolymer is precipitated or coagulated by controlled cooling to form the membrane. The membrane, once formed, can be subjected to membrane conditioning or pretreatment, prior to its end-use. The conditioning or pretreatment can be thermal annealing to relieve stresses or pre-equilibration in the expected feed stream.

A porous asymmetric membrane is made by the method comprising: dissolving a hydrophobic polymer comprising, consisting essentially of, or consisting of a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric membrane.

The porous asymmetric membrane exhibits many advantageous surface properties. The polymer additive is incorporated into the selective surface layer of the porous asymmetric membrane by the method, which advantageously reduces the water contact angle of the surface compared to a porous asymmetric membrane made from the hydrophobic polymer without the polymer additive. For example, the porous asymmetric membrane can have a water contact angle of greater than or equal to 20, 30, or 40 degrees, and less than or equal to 80, 70, or 60 degrees. In some embodiments, the porous asymmetric membrane has a water contact angle of 40 to 80 degrees. The porous asymmetric membrane made by the method can have a mean surface pore size distribution on the selective layer of greater than or equal to 1, 5, 10 nanometers (nm) and less than or equal to 100, 50, or 20 nm±1, 2, 5, or 10 nm. The porous asymmetric membrane made by the method can also have a surface pore density of greater than or equal to 100, 200, or 400 pores per $\mu m^2$ and less than or equal to 4,000, 2,400, or 1,200 pores per $\mu m^2$.

The method is also applicable to making hollow fibers by coextrusion of a dope solution and a bore fluid, in which the membrane-forming composition is the dope solution and the first non-solvent composition is the bore fluid. Thus in some embodiments, a method of making a hollow fiber by coextrusion through a spinneret comprising an annulus and a bore, comprises coextruding coextruding: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber.

In some embodiments the method further comprises washing the hollow fiber in a third non-solvent composition. This step serves to rinse any residual water-miscible polar aprotic solvent from the hollow fibers. The second and third non-solvent compositions can be the same or different, and can comprise water, or a mixture of water and a water-miscible polar aprotic solvent. In some embodiments the first and second non-solvent compositions are independently selected from water, and a mixture of water and N-Methyl-2-pyrrolidone. In some embodiments, the second and third non-solvent compositions are each water. The water can be deionized. In some embodiments, the method further comprises drying the follow fiber to remove residual first and second non-solvent composition, for example water and N-methyl-2-pyrrolidone.

A hollow fiber is made by coextruding through a spinneret comprising an annulus and a bore: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber.

The hollow fibers can be used in various separation modules. Thus in some embodiments, a separation module comprises hollow fiber made by coextruding through a spinneret comprising an annulus and a bore: a membrane-forming composition comprising a hydrophobic polymer comprising a poly(phenylene ether), poly(phenylene ether) copolymer, polyethersulfone, polysulfone, polyphenylsulfone, polyimide, polyetherimide, or a combination comprising at least one of the foregoing, through the annulus, and a first non-solvent composition comprising water, a water-miscible polar aprotic solvent, or a combination comprising at least one of the foregoing, and a polymer additive dissolved in the first non-solvent composition, through the bore, into a second non-solvent composition comprising water, a water-miscible polar aprotic solvent, or a combination comprising at least one of the foregoing, to form the hollow fiber.

The configuration of the porous asymmetric membrane made by the method can be sheet, disc, spiral wound, plate and frame, hollow fiber, capillary, or tubular. Outside-in and inside-out separations are applicable to hollow fiber membranes, capillary membranes, and tubular membranes, each having an inner and outer surface in contact with the feed and retentate or the permeate.

The porous asymmetric membrane made by the method can be a porous hollow fiber. The wall thickness of the hollow fiber can be 20 to 100 nanometers. Within this range, the diameter can greater than 30 and less than or equal to 80, 60, 40, or 35 nanometers. In another embodiment the diameter can be 50 to 3000 a micrometers (μm), specifically 100 to 2000 μm. The membrane can comprise a substantially non-porous surface layer, and the non-porous surface layer can be on the inside surface of the hollow fiber. A separation module can comprise bundles of porous hollow fibers. In some embodiments, the fiber bundle comprises 10 to 10,000 porous hollow fibers. The hollow fibers can be bundled longitudinally, potted in a curable resin on both ends, and encased in a pressure vessel to form the hollow fiber module. Hollow fiber modules can be mounted vertically or horizontally.

The porous asymmetric membranes can be fabricated into separation modules designed for purification of various aqueous, non-aqueous (e.g., hydrocarbon), or gaseous streams. Thus in some embodiments, a separation module comprises the porous asymmetric membrane comprising, consisting essentially of, or consisting of: a hydrophobic polymer comprising, consisting essentially of, or consisting of a poly(phenylene ether) or poly(phenylene ether) copolymer and a polymer additive. The separation module can be designed for dead-end separation, cross-flow separation, inside-out separation, or outside-in separation.

Depending upon porous asymmetric membrane surface pore size distribution and pore density, and the end-use, the separation module fabricated from the porous asymmetric membrane made by the method can be a media filtration module, a microfiltration module, an ultrafiltration module, a nanofiltration module, or a reverse osmosis module. The separation module fabricated from the porous asymmetric membrane made by the method can also be a membrane contactors module, a pervaporation module, a dialysis module, an osmosis module, an electrodialysis module, a membrane electrolysis module, an electrophoresis module, or a membrane distillation module. For media filtration, the surface pore size can be about 100 to about 1,000 micrometers. For microfiltration, the surface pore size can be about 0.03 to about 10 micrometers. For ultrafiltration, the surface pore size can be about 0.002 to 0.1 micrometers. For nanofiltration, the surface pore size can be about 0.001 to about 0.002 micrometers. The porous asymmetric membranes described herein are surprisingly well suited for ultrafiltration and nanofiltration. In some embodiments, the porous asymmetric membrane has a surface pore size of 0.001 to 0.05 micrometers (μm), specifically 0.005 to 0.01 μm.

The molecular weight cut off (MWCO) of a membrane is the lowest molecular weight solute in which 90 weight percent (wt %) or greater of the solute is retained by the membrane. The porous asymmetric membranes made by the method can have a MWCO of 500 to 20,000 daltons (Da), specifically 1,000 to 10,000 Da, more specifically 2,000 to 8,000 Da, or still more specifically 3,000 to 7,000 Da. Furthermore, any of the foregoing MWCO ranges can be present in combination with a desirable permeate flux, such as clean water permeate flux (CWF). For example, the permeate flux can be 1 to 200, specifically 2 to 100, more specifically 4 to 50 L/(h·m²·bar), wherein L is liters and m² is square meters. The porous asymmetric membranes made by the method can also provide a CWF of about 10 to about 80 L/(h·m²·bar), about 20 to about 80 L/(h·m²·bar), or about 40 to about 60 L/(h·m²·bar).

Flux across the membrane is driven by the osmotic or absolute pressure differential across the membrane, referred to herein as the trans-membrane pressure (TMP). The trans-membrane pressure can be 1 to 500 kilopascals (kPa), specifically 2 to 400 kPa, and more specifically 4 to 300 kPa.

The porous asymmetric membranes made by the method are useful for treatment of a variety of aqueous streams. Depending upon surface pore size distribution and pore density, and the configuration of the porous asymmetric membrane, the porous asymmetric membrane can be used to remove one or more of the following contaminants from water: suspended matter, particulate matter, sands, silt, clays, cysts, algae, microorganisms, bacteria, viruses, colloidal matter, synthetic and naturally occurring macromolecules, dissolved organic compounds, and salts. Thus, separation modules fabricated from the porous asymmetric membranes made by the method can be used in wastewater treatment, water purification, food processing, and in the dairy, biotechnology, pharmaceutical, and healthcare industries.

The porous asymmetric membranes made by the method, and separation modules fabricated from the porous asymmetric membranes made by the method, can advantageously be used in medical, pharmaceutical, biotechnological, or food processes, for example the removal of salts and/or low molecular weight organic impurities from aqueous streams by ultrafiltration, which results in increased concentration of a material having a molecular weight above the cut-off of the porous asymmetric membrane in an aqueous stream. The aqueous stream can be human blood, animal blood, lymph fluids, microbial or cellular suspensions, for example suspensions of bacteria, alga, plant cells, or viruses. Specific medical applications include the concentration and purification of peptides in blood plasma; hemofiltration; hemodialysis; hemodiafiltration; and renal dialysis. Other applications include enzyme recovery and desalting of proteins. Specific food applications include ultrafiltration of meat products and by-products, plant extracts, suspensions of algae or fungi, vegetable food and beverages containing particles such as pulp, and the production of milk protein concentrate for the production of cheese. Other applications include downstream processing of fermentation broths; concentration of protein in whole egg or egg white with simultaneous removal of salts and sugars; and concentration of gelling agents and thickeners, for example agar, carrageenan, pectin, or gelatin. Since a separation module fabricated from the porous asymmetric membrane made by the process is useful for a wide variety of aqueous fluid separation applications in many different fields, it may be applicable to other fluid separation problems not expressly disclosed herein as well.

Separation modules fabricated from the porous asymmetric membrane made by the method can be used for liver dialysis or hemodialysis; separation of polysaccharides, wherein separation comprises contacting a mixture of sugars, such as dextrose, glucose and fructose, with the asymmetric porous membrane to provide a product stream enriched in a desired sugar; protein or enzyme recovery; the production of purified water, e.g., drinking water; pretreatment of water in desalination systems; removal of contaminants, including biological contaminants such as bacteria or protozoa, or organic chemical contaminants such as polychlorinated biphenyls (PCBs), to produce a purified product stream; oxygenation of blood, such as in an artificial lung device; wastewater treatment; or membrane distillation.

The invention includes at least the following embodiments.

Embodiment 1

A porous asymmetric membrane, comprising, consisting essentially of, or consisting of: a hydrophobic polymer comprising, consisting essentially of, or consisting of a poly(phenylene ether) or poly(phenylene ether) copolymer; and a polymer additive.

Embodiment 2

The porous asymmetric membrane of embodiment 1, wherein the hydrophobic polymer comprises a poly(phenylene ether) copolymer comprising first and second repeat units having the structure:

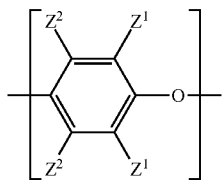

wherein each occurrence of $Z^1$ is independently halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy, wherein at least two carbon atoms separate the halogen and oxygen atoms; wherein each occurrence of $Z^2$ is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy, wherein at least two carbon atoms separate the halogen and oxygen atoms; and wherein the first and second repeat units are different.

Embodiment 3

The porous asymmetric membrane of embodiment 1 or 2, wherein the hydrophobic polymer comprises a poly(phenylene ether) copolymer comprising, consisting essentially of, or consisting of: 80 to 20 mole percent repeat units derived from 2,6-dimethylphenol; and 20 to 80 mole percent repeat units derived from a first monohydric phenol having the structure

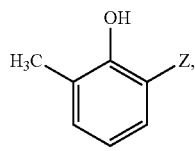

wherein Z is $C_1$-$C_{12}$ alkyl or cycloalkyl, or a monovalent radical having the structure

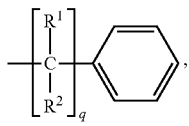

wherein q is 0 or 1, and $R^1$ and $R^2$ are independently hydrogen or $C_1$-$C_6$ alkyl; wherein the poly(phenylene ether) copolymer has an intrinsic viscosity of 0.7 to 1.5 deciliters per gram, measured in chloroform at 25° C.

Embodiment 4

The porous asymmetric membrane of any of embodiments 1-3, wherein the polymer additive is a hydrophilic polymer or an amphiphilic polymer.

Embodiment 5

The porous asymmetric membrane of any of embodiments 1-4, wherein the polymer additive comprises poly(vinyl pyrrolidone), poly(oxazoline), poly(ethylene glycol), poly(propylene glycol), a poly(ethylene glycol) monoether or monoester, a poly(propylene glycol) monoether or monoester, a block copolymer of poly(ethylene oxide) and poly(propylene oxide), polystyrene-graft-poly(ethylene glycol), polystyrene-graft-poly(propylene glycol), polysorbate, cellulose acetate, or a combination comprising at least one of the foregoing.

Embodiment 6

The porous asymmetric membrane of any of embodiments 1-5, wherein the polymer additive comprises an amphiphilic block copolymer comprising a hydrophobic block and a hydrophilic block or graft.

Embodiment 7

The porous asymmetric membrane of embodiment 6, wherein the hydrophobic block comprises polystyrene and the hydrophilic block or graft comprises poly(N,N-dimethylacrylamide) or poly(4-vinylpyridine).

Embodiment 8

A porous asymmetric membrane, comprising: a poly(phenylene ether) copolymer comprising 80 to 20 mole percent repeat units derived from 2,6-dimethylphenol; and 20 to 80 mole percent repeat units derived from 2-methyl-6-phenylphenol; and a polymer additive comprising poly(vinylpyrrolidone), poly(styrene-co-vinylpyrrolidone), polystyrene-block-poly(N,N-dimethylacrylamide) or a combination comprising as least one of the foregoing.

Embodiment 9

The porous asymmetric membrane of any of embodiments 1-8, having a contact angle of 40 to 80 degrees.

Embodiment 10

A method of forming a porous asymmetric membrane, the method comprising: dissolving a hydrophobic polymer comprising, consisting essentially of, or consisting of a poly(phenylene ether) or poly(phenylene ether) copolymer and, a polymer additive in a water-miscible polar aprotic solvent to form a porous asymmetric membrane-forming composition; and phase-inverting the porous asymmetric membrane forming-composition in a first non-solvent composition to form the porous asymmetric membrane.

Embodiment 11

The method of embodiment 10, further comprising washing the porous asymmetric membrane in a second non-solvent composition.

Embodiment 12

The method of embodiment 10 or 11, further comprising drying the porous asymmetric membrane.

Embodiment 13

The method of any of embodiments 10-12, wherein the first non-solvent composition comprises 10 to 100 weight percent water and 0 to 90 weight percent N-methyl-2-pyrrolidone, based on the total weight of the first non-solvent composition.

Embodiment 14

A method of making a hollow fiber by coextrusion through a spinneret comprising an annulus and a bore, wherein the method comprises coextruding: a membrane-forming composition comprising a hydrophobic polymer comprising a poly(phenylene ether) or poly(phenylene ether) copolymer, and a polymer additive dissolved in a water-miscible polar aprotic solvent through the annulus, and a first non-solvent composition comprising water, a water-miscible polar aprotic solvent, or a combination comprising at least one of the foregoing, through the bore, into a second non-solvent composition comprising water, a water-miscible polar aprotic solvent, or a combination comprising at least one of the foregoing, to form the hollow fiber.

Embodiment 15

The method of embodiment 14, further comprising washing the hollow fiber in a third non-solvent composition.

Embodiment 16

The method of embodiment 14 or 15, further comprising drying the hollow fiber.

Embodiment 17

A separation module comprising the porous asymmetric membrane of any of embodiments 1-9.

Embodiment 18

A hollow fiber made by the method of any of embodiments 14-16.

Embodiment 19

A separation module comprising the hollow fiber of embodiment 18.

Embodiment 20

The porous asymmetric membrane of embodiment 3, wherein the first monohydric phenol is 2-methyl-6-phenylphenol.

Embodiment 21

The porous asymmetric membrane of any of embodiments 1-9 and 21, wherein the hydrophobic polymer has an intrinsic viscosity of 0.7 to 1.5 deciliters per gram, measured in chloroform at 25° C.

Embodiment 22

The method of any of embodiments 10-16, wherein the solubility of the hydrophobic polymer in the water-miscible polar aprotic solvent is 50 to 400 grams per kilogram at 25° C., based on the combined weight of the poly(phenylene ether) copolymer and the solvent.

Embodiment 23

The porous asymmetric membrane of embodiment 6 or 7, wherein the amphiphilic block copolymer comprises 20 to 50 weight percent of the hydrophobic block and 50 to 80 weight percent of the hydrophilic block or graft.

Embodiment 24

The porous asymmetric membrane of embodiment 6, wherein the hydrophilic block or graft comprises poly(ethylene oxide) or a copolymer of ethylene oxide with 1,2-propylene oxide, 1,2-butylene oxide, styrene oxide, or a combination comprising at least one of the foregoing.

Embodiment 25

The porous asymmetric membrane of embodiment 6, wherein the hydrophilic block or graft comprises an addition polymer of methoxy-capped poly(ethylene oxide) methacrylate, 4-vinylpyridine, N-vinylpyrrolidone, N,N-dimethylacrylamide, 4-acryloylmorpholine, or a combination comprising at least one of the foregoing.

Embodiment 26

The porous asymmetric membrane of embodiments 1-9, 20-21, and 23-25, wherein the hydrophobic polymer further comprises poly(2,6-dimethyl-1,4-phenylene ether), polyethersulfone, polysulfone, polyphenylsulfone, or a combination comprising at least one of the foregoing.

Embodiment 27

A porous asymmetric membrane made by the method of any of embodiments 10-16.

Embodiment 28

The porous asymmetric membrane of embodiment 27, having a contact angle of 40 to 80 degrees.

Embodiment 29

The porous asymmetric membrane of any of embodiments 1-9, 20-21, and 23-28, wherein a configuration of the porous asymmetric membrane is a sheet, disc, spiral wound, plate and frame, hollow fiber, capillary, or tubular.

Embodiment 30

The porous asymmetric membrane of any of embodiments 1-9, 20-21, and 23-29, wherein the membrane is a porous asymmetric flat sheet.

Embodiment 31

The porous asymmetric membrane of any of embodiments 1-9, 20-21, and 23-30, wherein the asymmetric membrane is in the form of a spiral.

Embodiment 32

The porous asymmetric membrane of any of embodiments 1-9, 20-21, and 23-30, wherein the membrane is a porous asymmetric hollow fiber.

Embodiment 33

A separation module comprising the porous asymmetric membrane of any of embodiments 1-9, 20-21, and 23-32.

The invention is further illustrated by the following non-limiting examples.

Preparative Examples: Synthesis of MPP-DMP Copolymers

The copolymerizations were conducted in a bubbling polymerization reactor equipped with a stirrer, temperature control system, nitrogen padding, oxygen bubbling tube, and computerized control system. There were also feeding pot and pump for dosing reactants into the reactor.

TABLE 1

Materials

| Abbreviation | Chemical Name |
|---|---|
| DMP | 2,6-Dimethylphenol |
| MPP | 2-Methyl-6-phenylphenol |
| DBA | Di-n-butylamine |
| DBEDA | N,N'-Di-tert-butylethylenediamine |
| DMBA | N,N-Dimethylbutylamine |
| QUAT | Didecyldimethyl ammonium chloride |
| NTA | Nitrilotriacetic acid |
| CAT | Solution of $Cu_2O$ in concentrated HBr, 6.5 wt. % Cu |
| NMP | N-Methyl-2-pyrrolidone, available from ThermoFisher. |
| 6020P | A polyethersulfone (PES), available from BASF as ULTRASON ™ E 6020 P. |
| PES | A polyethersulfone, available from BASF as ULTRASON ™ E 6020 P. |
| PVP K30 | Poly(vinyl pyrrolidone) having a K value of 26-35, calculated for a 1% aq. solution by the Finkentscher equation; and available from Aldrich. |
| PVP K90 | Poly(vinyl pyrrolidone) having a K value of 90-100, calculated for a 1% aq. solution by the Finkentscher equation; and available from Aldrich. |

Preparative Example 1: Preparation of MPP-DMP Copolymer with 50 Mole Percent MPP in 1.8-Liter Reactor Toluene (622.88 grams), DBA (8.1097 grams), DMBA (30.71 grams), and 5.44 grams of a diamine mix consisting of 30 weight percent (wt. %) DBEDA, 7.5 weight percent QUAT, and the balance toluene, were charged to a bubbling polymerization reactor and stirred under a nitrogen atmosphere at 25° C. A mix of 6.27 grams HBr and 0.5215 grams $Cu_2O$ was added. Oxygen flow to the vessel was begun after 4 minutes of monomer mixture addition. The reactor temperature was ramped to 40° C. in 18 min, maintained at 40° C. for 57 min, ramped to 45 C in 11 min, maintained at 45° C. for 33 min and ramped to 60° C. in 10 min. 403.67 grams of monomer solution (20.3 wt. % DMP, 30.6 wt. % MPP and 49. 1 wt. % toluene) was added over 35 minutes. Oxygen flow was maintained for 115 minutes, at which point the oxygen flow was stopped and the reaction mixture was immediately transferred to a vessel containing 11.07 grams NTA salt and 17.65 grams DI (deionized) water. The resulting mixture was stirred at 60° C. for 2 hours, and the layers were then allowed to separate. The decanted light phase was precipitated in methanol, filtered, reslurried in methanol, and filtered again. The copolymer was obtained as a dry powder after drying in a vacuum oven under nitrogen blanket at 110° C.

Preparative Examples 2-4: Preparation of MPP-DMP Copolymers with 20, 50, and 80 Mole % MPP with IV's of ~1 Deciliter Per Gram The process of Preparative Example 1 was scaled to a one gallon steel bubbling reactor and copolymerization was conducted in similar fashion as described above. The ingredients for the batch reactor charges and continuous monomer feed solution are shown in Table 2. After charging the reactor the contents were brought with stirring to 25° C. before starting the continuous feed of monomer in toluene and then oxygen feed. The monomer/toluene mixture was fed over 45 minutes, and oxygen feed was maintained until 130 minutes. The reactor temperature was ramped to 45° C. at 90 minutes and then ramped to 60° C. at 130 minutes. The reaction contents were then transferred to a separate vessel for addition of NTA to chelate the copper, followed by separation of the toluene solution from the aqueous phase in centrifuge, precipitation of the copolymer solution into methanol as described above.

TABLE 2

Material Amounts for Preparative Examples 2-4

| | Example 2 | Example 3 | Example 4 |
|---|---|---|---|
| Raw Material (g) | | | |
| MPP/DMP (mole ratio) | 20/80 | 50/50 | 80/20 |
| CAT | 17.3 | 21.6 | 17.3 |
| DBEDA | 5.3 | 6.7 | 5.3 |
| DBA | 9.9 | 9.9 | 9.9 |
| DMBA | 34.3 | 33.3 | 32.5 |
| QUAT | 1.6 | 2.0 | 1.6 |
| DMP/TOLUENE 50/50 | 29.5 | 18.5 | 5.5 |
| TOLUENE | 2961.0 | 2961.0 | 2961.0 |
| MPP | 5.6 | 14.0 | 16.0 |
| Continuous Feed Solution | | | |
| DMP/TOLUENE 50/50 | 364.5 | 228 | 64 |
| MPP | 69.4 | 172 | 197 |
| Total | 3498.36 | 3466.925 | 3310.08 |

The dried copolymers were characterized for molecular weight distribution via gel permeation chromatography (GPC) using $CHCl_3$ as solvent and referenced to polystyrene standards. Intrinsic viscosity (IV) was measured in $CHCl_3$ solution at 25° C., using an Ubbelohde viscometer, and is expressed in units of deciliters per gram (dL/g). The glass transition temperature Tg was measured using differential scanning calorimetry (DSC) and expressed in ° C. The results for examples 1-4 are summarized in Table 3. "Mn" refers to number average molecular weight, "Mw" refers to weight average molecular weight, "D" refers to polydispersity, and "g" refers to grams.

TABLE 3

Characterization of MPP-DMP Copolymers of Preparative Examples 1-4

| Ex. No. | Scale | MPP/DMP (mole/mole) | GPC Mn (g/mole) | GPC Mw (g/mole) | GPC D (Mw/Mn) | IV in $CHCl_3$ (dL/g) | Tg ° C. |
|---|---|---|---|---|---|---|---|
| 1 | 1.8 liter | 50/50 | 20,213 | 219,130 | 10.8 | 0.83 | 185 |
| 2 | 1 gallon | 20/80 | 50,310 | 172,100 | 3.4 | 1.04 | 210 |
| 3 | 1 gallon | 50/50 | 39,820 | 194,900 | 4.9 | 0.97 | 187 |
| 4 | 1 gallon | 80/20 | 22,620 | 241,000 | 10.7 | 0.96 | 177 |

Examples 5-10: General Procedure for Casting Membranes Via Solvent/Non-Solvent Phase Inversion Process In general, porous, asymmetric membranes were cast by dissolving MPP-DMP copolymers in NMP at concentrations of around 16 wt. %; pouring the viscous casting solution onto a glass plate and drawing a thin film 150-250 micrometers thick across the plate by means of a casting knife. The glass plate bearing the thin film of MPP-DMP in NMP was placed into a primary coagulation bath over a time period of 10-15 minutes. The primary coagulation bath was a mixture of NMP and water, and promoted the precipitation and coagulation of the copolymer into an asymmetric porous membrane. The coagulated copolymer film floated free of the glass plate when coagulation was substantially complete, at which time it was transferred to a second bath in which it was soaked and rinsed in clean water to remove residual NMP.

The process is described in more detail as follows. The test copolymer was dissolved in N-methyl-2-pyrrolidone (NMP), chromatography grade, totaling 8-10 grams in a 20 milliliter (mL) glass vial, sealed tightly, and placed on a low speed roller for 13-48 hours until it forms a homogenous solution. The solution was poured in an oblong puddle and an adjustable height doctor blade was used to drag across the glass plate at a constant speed by hand. The entire glass plate bearing the cast copolymer solution was fully submerged into an initial non-solvent bath (25-100 wt. % DI water in NMP) until the membrane begins to lift off the plate. The membrane was transferred off of the glass plate into the intermediate non-solvent bath of 100 wt. % DI water and weighed down at the corners with glass stoppers to allow the exchange of NMP into the water bath. After 15-45 minutes the membrane was transferred to a final non-solvent bath of 100 wt. % water to fully solvent exchange the pores overnight, also weighed down to submerge fully. The membrane was dried at room temperature. Characterization was performed on pieces cut from the center and most uniform portion of the membrane. The viscosity of the copolymer solutions in NMP was measured at 20° C. using a Brookfield RDV-III Pro viscometer equipped with a small-sample adapter and cylindrical spindle.

Characterization of Membranes

A simple estimate of the water flow through the membranes was made by cutting a 47-millimeter (mm) circle of the membrane and placing it on a fritted funnel and clamped. The vacuum filter flask was tared on a balance then 100 g of water was added to the fritted funnel and one atmosphere vacuum was applied for 15-60 min. (minutes). All data were normalized to a 60-min. run time. The water flow was calculated by placing the vacuum filter flask on the tared balance and recording the value.

The surface porosities and cross-sectional morphologies of the membranes were characterized using Carl Zeiss Supra VP scanning electron microscopy (SEM). The "top" membrane surfaces (those that were first in contact with the NMP/water bath) were imaged for selective surface morphology. The membrane samples were coated with ~0.3 nm Pt/Pd target using Cressington 208 high resolution sputter coater equipped with thickness controller MTM-20. The surface morphology was imaged using low voltage capability (≤5 kV, probe current 200 nA and inlens surface sensitive detection mode at 100,000× magnifications. A minimum of 3 images were combined for digital image analysis using Clemex Vision PE 6.0.035 software to estimate the pore size distributions and pooled for the analysis. Samples for cross-sectional imaging were soaked in ethanol for 5 minutes and cryo-fractured using liquid nitrogen, then allowed to come to room temperature and dried in air. The cryo-fractured membrane samples were coated with Pt/Pd target and imaged using SEM for cross sectional morphology.

The interaction of the membrane surfaces with water was quantified via measurement of contact angle using a Kruss DA-25 drop shape analysis system. A small square section of membrane was cut out from the center of the membrane, and mounted on a glass microscope slide using double sided tape. A 2-microliter water droplet was deposited on the surface and the drop shape was measured using digital curve fitting 5 times with a 1 second spacing and the resulting contact angles of the water droplet with the membrane surface were averaged together.

Examples 9-10: Membranes Cast from 20/80 MPP-DMP Copolymer with PS-PEO Diblock Copolymer A sample of an amphiphilic block diblock copolymer was obtained from Sigma-Aldrich, which is described in their catalog as being comprised of a block of polystyrene (PS) having an Mn of about 30,000 g/mole, which has been coupled to a block of poly(ethylene oxide) (POE) of Mn of about 1,000 g/mole. From this description we conclude that this PS/PEO block copolymer contains only about 3 wt. % of hydrophilic block by weight. In Examples 9 and 10, solutions containing 16 wt. % of the 20/80 MPP-DMP copolymer of Example 2 were prepared in the presence of 2 and 4 wt. % of the PS/PEO diblock copolymer, respectively, and cast into membranes following the same procedures as described above. The results of SEM image analysis of these membranes are presented in FIG. 1. The surface appearance of the membranes characterized by SEM were found to be very similar to that of Example 6 which was prepared by casting the MPP-DMP copolymer alone.

The blends of Examples 9-10 containing PS/PEO copolymer yielded membrane surfaces upon phase-inversion casting which had pore size distributions that showed as good or better consistency in pore size distribution as seen for Example 6, which was made from MPP-DMP copolymer alone (Table 6). From this we can conclude that the presence of short blocks of PS has not substantially disrupted the inherently good membrane-forming characteristics of the MPP-DMP copolymer. The contact angle of the membranes containing the PS-PEO diblock as additive show a slight trend towards reduced contact angle, and a decrease in Tg which most likely results from forming a miscible blend between the MPP-DMP copolymer and the PS blocks of the diblock copolymer. It is expected that this type of additive will not be soluble in NMP/water, contrary to PVP, and so it would be expected to be present in the membrane itself.

TABLE 6

Properties of Membranes Made from Blends of MPP-DMP Copolymer and PS/PEO Diblock Copolymer

| Ex. No. | Wt % Resin In NMP Casting Dope | Surface Pore Size Distribution of Membrane (μm) | Membrane Tg (° C.) |
|---|---|---|---|
| 6 | 16% Ex. 2 | 12.2 ± 3.8 | 210 |
| 9 | 16% Ex. 2 + 2% PS-PEO | 10.1 ± 2.0 | 183 |
| 10 | 16% Ex. 2 + 4% PS-PEO | 9.2 ± 1.7 | 176 |

Preparative Examples 11-13: Preparation of MPP-DMP Copolymers with 20, 50, and 80 Mole Percent MPP MPP-DMP copolymers with 20, 50, and 80 mole % MPP were prepared in a 1-gallon reactor using the same methods as in Preparative Examples 2-4. The dried copolymers were characterized for molecular weight distribution as described above for Preparative Examples 2-4. The results for Preparative Examples 11-13 are summarized in Table 7. "Mn" refers to number average molecular weight, "Mw" refers to weight average molecular weight, "D" refers to polydispersity, and "g" refers to grams.

TABLE 7

Characterization of MPP-DMP Copolymers of Preparative Examples 11-13

| Ex. No. | MPP/DMP (mole/mole) | GPC Mn (g/mole) | GPC Mw (g/mole) | GPC D (Mw/Mn) | IV in CHCl$_3$ (dL/g) |
|---|---|---|---|---|---|
| 11 | 20/80 | 63,010 | 210,800 | 3.3 | 1.14 |
| 11a | 20/80 | 49,940 | 199,700 | 4.0 | 1.08 |
| 12 | 50/50 | 42,460 | 216,200 | 5.1 | 0.98 |
| 13 | 80/20 | 36,490 | 310,700 | 8.5 | 1.08 |

Examples 14-16: Casting of Membranes Via Solvent/Non-Solvent Phase Inversion Process Membranes were cast using the same procedures as described for Examples 5-10, except that the temperature was controlled to be 35° C. throughout the casting and initial phase-inversion coagulation process. The vials of copolymer solutions in NMP were equilibrated for several hours in a milled aluminum "dry block" which was controlled at 35.0±0.1° C. by use of an electric heater. The glass casting plates and casting knife were equilibrated for several hours atop an electrically-heated hot plate at 35.0±0.1° C. before use. The NMP/water coagulation solution of 2 liters was contained in a digitally-controlled thermostat bath at 35.0±0.1° C. Additionally the viscosity of the copolymer solutions in NMP was measured using a Brookfield LVDV3T viscometer equipped with a cone & plate measuring heat and circulating water bath, controlled to within 0.1° C. of the desired temperature.

Figure 4:
FIG. 4 depicts laboratory-scale hollow fiber membrane modules.

Membranes were cast at 35° C. and characterized for surface pore size distribution and cross-sectional structure by SEM, the results of which are provided in Table 8 and in FIG. 4. The solution viscosity data again shows a trend towards lower viscosity as MPP co-monomer content is increased as seen at lower temperatures in Table 4. A strong correlation between the amount of MPP co-monomer and the formation of macrovoids in the cross-section of the membranes is observed.

TABLE 8

Membranes cast from MPP-DMP copolymers into 30/70 NMP/water at 35° C.

| | NMP Casting Dope | | Membrane Properties | | |
|---|---|---|---|---|---|
| Ex. No. | Wt % Resin | Viscosity (cP at 35° C.) | Surface Pore Size Distribution (nm) | Surface Pore Density (pores per μm$^2$) | Extent of Macrovoid Formation |
| 14 | 16% Ex. 11 | 6,838 | 11.4 ± 3.0 | 508 | Very low |
| 15 | 16% Ex. 12 | 1,474 | 10.4 ± 2.4 | 607 | Moderate |
| 16 | 16% Ex. 13 | 909 | 9.7 ± 1.9 | 476 | high |

Example 17 and Comparative Example 2: Comparison of PES/PVP and 50/50 MPP-DMP Membranes To facilitate comparison, the membrane of Example 17 was prepared using the 50/50 MPP-DMP copolymer of Example 12 and the procedure of Example 15, except that the concentration of the copolymer was increased to 18% by weight in order to better match the expected viscosity of Comparative Example 2.

The solution viscosities measured at 20° C. of Comparative Example 2 and Example 17 were similar but not quite as high as stated in Table 9 of International Application Publication WO 2013/131848. Because the membrane castings were to be conducted at 35° C., the solution viscosities were measured at that temperature and the viscosity of Example 17 was found to be significantly higher than the Comparative Example 2. Because of differences in the temperature sensitivity between a PES/PVP blend and a single MPP-PPE copolymer in NMP, no further adjustments to solution viscosity were made.

Figure 2:
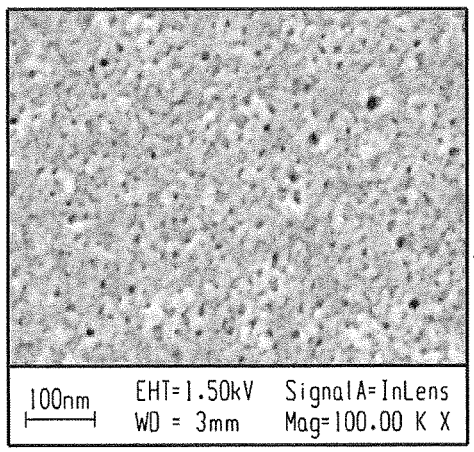
FIG. 2 depicts SEM images of the asymmetric membranes of Example 17 and Comparative Example 2.
Figure 2:
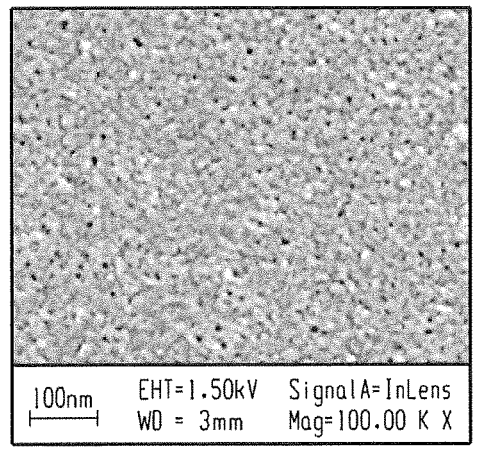
Figure 2:
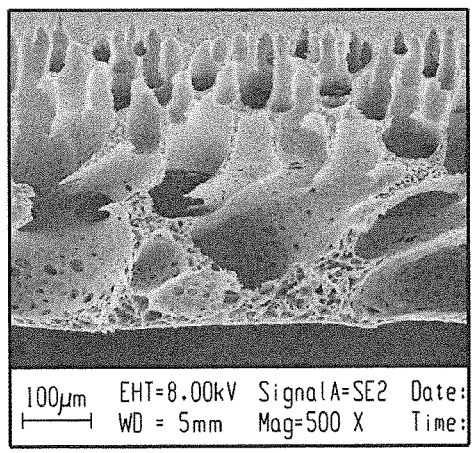
Figure 2:
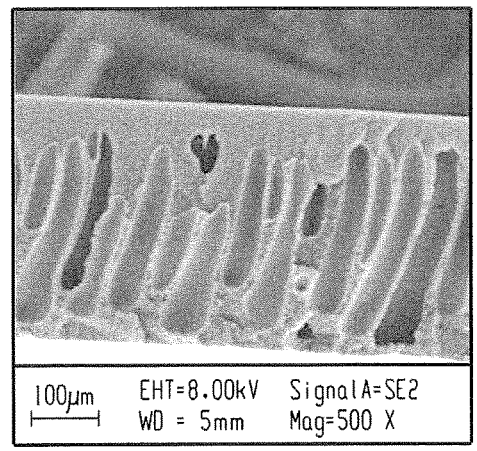

Flat membranes were cast from these solutions at 35° C. according to the procedure of Example 1 in the '848 application. The dried membranes were characterized by SEM, the results of which are shown in FIG. 2. The characteristics of the membranes are provided in Table 9. The membranes of Comparative Example 2 have a much higher degree of macrovoid formation, larger mean surface pore sizes and lower pore density than those of Example 17.

double orifice spinneret and after passing the air gap, immersed into the water coagulation bath. The take-up velocity was controlled by a pulling wheel, which enabled also stretching of the fiber. A solution of MPP-DMP copolymer according to Example 12 of 18% by weight in NMP was successfully spun into hollow PPE fibers to produce Example 18 using the same apparatus and the same conditions as used to prepare Comparative Example 3.

A summary of the fiber spinning conditions, spinneret geometry, and measured dimensions of the dried hollow fibers is shown in Table 10. For Comparative Example 3, the rinsing bath was held at 65° C. according to the example in the '848 application, which is understood to be for rinsing away excess PVP from the surface of the hollow fiber membrane. For Examples 18-20, which were prepared from the 20/80, 50/50, and 80/20 MPP-PPE copolymers, respec-

TABLE 9

Flat Membranes Cast According to the Conditions of the '848 Application.

| | | NMP Casting Dope | | Membrane | | |
|---|---|---|---|---|---|---|
| Ex. No. | Wt % Resin | Viscosity (cP at 20° C.) | Viscosity (cP at 35° C.) | Surface Pore Size Distribution (nm) | Surface Pore Density (pores per $\mu m^2$) | Extent of Macrovoid Formation |
| C2 | 14% 6020P/ 5% K30/ 2% K90/ 3% $H_2O$ | 5,764 | 1,858 | 11.3 ± 3.0 | 1,803 | High |
| 17 | 18% Ex. 12 | 4,386 | 3,270 | 9.9 ± 2.1 | 2200 | Moderate |

Examples 18-20 and Comparative Example 3: Hollow Fiber Spinning

The membrane-forming compositions (NMP casting dopes) of Examples 14-16, (containing the MPP-DMP copolymers of Examples 11-13, respectively) and Comparative Example 2 were processed into hollow fiber membranes according to the methods disclosed in the '848 application. ULTRASON™ E 6020P (BASF) was maintained for 24 hrs. under vacuum prior to mixing to remove all moisture. The chemicals were mixed in a glass bulb until a homogenous solution was reached. Before filling the spinning solution into the spinning set up, the composition was filtered through a 25 µm metal mesh to remove any residual particles in the composition. The spinning solution was degassed for 24 hrs. before the spinning. For all spinnings, a bore solution of 70 wt % deionized water and 30 wt % NMP was prepared and was degassed for 24 hrs. before use.

Figure 3:
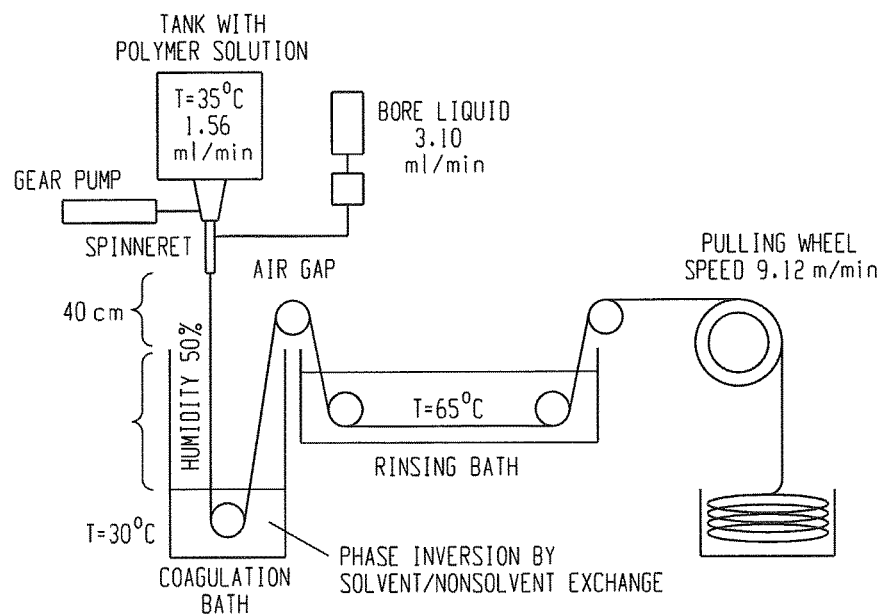
FIG. 3 depicts a diagram of a laboratory scale, dry-wet immersion precipitation hollow fiber spinning apparatus.

Hollow fiber membranes of PES and PVP (Comparative Example 3) were prepared on a laboratory scale by dry-wet immersion precipitation spinning using the apparatus shown in the schematic of FIG. 3 and under conditions adapted from the '848 application. The copolymer solution along with the bore liquid were simultaneously pumped through a tively, the rinsing bath was held at 30° C. for safety in handling the fibers and because there is no PVP to be washed away. The take-up velocity was adjusted such that the wall thickness of the two hollow fiber samples was in the range of 40-60 micrometers. The post treatment process for the hollow fiber produced was as described in the '848 application. The fibers were washed in 70° C. purified water for 3 hrs. After 1.5 h the water was exchanged. Afterwards the fibers were rinsed for another 24 hrs. in water at tap temperature. After the rinsing step, the fibers were hung in the lab to dry in air at ambient temperature.

Based on the finding that the membrane-forming polymer solution viscosity in NMP was very sensitive to the amount of MPP co-monomer in the copolymer, the concentration of each resin was adjusted so as to yield an essentially constant solution viscosity of just over 3,000 cP. As a result there is a direct correlation between the level of MPP co-monomer in the copolymer and the mass of PPE per unit length of fiber, with Example 18a demonstrating the most efficient use of resin under the same spinning conditions. The fiber wall thickness was also maintained to a greater extent in Ex. 19, suggesting that with further optimization of fiber spinning conditions to reduce the wall thickness, a greater reduction in mass per unit length can be realized.

TABLE 10

Summary of Process Conditions for Hollow Fiber Spinning and Fiber Properties

| | Comparative Example 3 | Ex. 18 | Ex. 19 | Ex. 20 |
|---|---|---|---|---|
| Wt % resin in NMP casting dope | 14% 6020P/ 5% K30/ 2% K90/ 3% H20 | 18% Ex. 12 | 14% Ex. 11 | 20% Ex. 13 |
| Viscosity (cP at 35° C.) | | 3270 | 3091 | 3137 |
| Dope temp. [° C.] | 35 | 35 | 35 | 35 |

TABLE 10-continued

Summary of Process Conditions for Hollow Fiber Spinning and Fiber Properties

|  | Comparative Example 3 | Ex. 18 | Ex. 19 | Ex. 20 |
|---|---|---|---|---|
| Die temp. [° C.] | — | — | — | — |
| Shaft temp. [° C.] | ~22 | ~30 | ~30 | ~22 |
| Shaft humidity [%] | 50 | 60 | 60-65 | 60 |
| Room humidity [%] | 35 | 40 | 40 | 40 |
| $1^{st}$ bath temp. [° C.] | 30 | 30 | 30 | 30 |
| $2^{nd}$ bath temp. [° C.] | 65 | 30 | 30 | 30 |
| Air Gap [cm] | 100 | 100 | 100 | 100 |
| Dope extrusion rate [mL/min] | 1.56 | 1.56 | 1.56 | 1.56 |
| Bore extrusion rate [mL/min] | 3.1 | 3.1 | 3.1 | 3.1 |
| Take up velocity [m/min] | 9.12 | 7.04 | 7.07 | 7.00 |
| Spinneret dimensions |  |  |  |  |
| Inner diameter [mm] | 0.4 | 0.4 | 0.4 | 0.4 |
| Outer diameter [mm] | 1.12 | 1.12 | 1.12 | 1.12 |
| Dry hollow fiber dimensions by SEM |  |  |  |  |
| Inner diameter [μm] | 445 | 605 | 510 | 605 |
| Wall thickness [μm] | 59 | 41 | 47 | 23 |
| Mass per km (g) | 25.9 | 40.2 | 31.1 | 43.3 |

Preparation of Hollow Fiber Membrane Modules

Lab scale hollow fiber membrane modules as shown in FIG. 4 were prepared for the clean water flux and molecular weight cut off measurements. 5-10 fibers, depending on the geometry were guided through polypropylene tubes and the t-connections, which provide access to the outer surface of the hollow fibers. Both ends were sealed with hot glue. After the glue hardened, the modules were carefully cut open at one or both ends to expose the inner core of the hollow fibers to make them ready to use. The membrane length was between 25 and 30 cm. The fibers of Ex. 20 were more brittle than the other fibers, and extra care was required to glue the fibers of Ex. 20 into the modules to avoid damaging the fibers.

Measurement of Clean Water Flux

Clean water flux (CWF) was measured as follows. A pump was connected to a mass flow controller and a pressure sensor. Behind the pressure sensor the membrane module was connected so that the filtration direction was inside-out, that is the water was forced into the bore side of the membrane and permeated through the membrane to the outside of the membrane. The filtration mode was dead end filtration, that is only one end of the filtration module was cut open and connected to the feed solution. The flow rate was set to 100 g/h and the feed pressure was recorded over time. After the pretreatment of the membrane modules, the experiment was run for 1 hr. to achieve steady state conditions.

Prior to the measurement, all the hollow fibers were wetted with a mixture of 50 wt % water and 50 wt % ethanol. Afterwards clean water was permeated through the hollow fiber membranes for 15 minutes to remove all residual ethanol from the fibers. The measurement was started directly after the pretreatment. The results of the water flux measurements are provided in Table 11.

TABLE 11

Clean Water Flux Measurements

| Ex. | Clean Water Flux (L/(h · m² · bar)) |
|---|---|
| CE3 (PES/PVP) |  |
| Module 1 | 8.0 |
| Module 2 | 8.6 |
| Module 3 | 7.9 |
| Module 4 | 9.1 |
| Average | 8.4 ± 0.6 |
| E18 (E12 - 20/80 MPP-DMP) |  |
| Module 1 | 44.3 |
| Module 2 | 24.9 |
| Module 3 | 64.8 |
| Module 4 | 60.1 |
| Module 5 | 54.4 |
| Average | 49.7 ± 15.8 |
| E19 (E11 - 50/50 MPP-DMP) |  |
| Average of 4 Modules | 40.2 ± 21 |
| E20 (E13 - 80/20 MPP-DMP) |  |
| Average of 3 Modules | 133 ± 18.5 |

As can be seen from Table 11, the highest clean water flux (133 L/(h·m²·bar)) was obtained at the highest MPP comonomer content—the 80/20 MPP-DMP copolymer of Ex. 20. Without being bound by theory, this effect may be due to the thinner fiber cross-section obtained with those fibers—a wall thickness of only 23 μm, as reported in Table 10. Although the individual values vary, the clean water flux for all the PPE copolymer fibers (Ex. 18-20) are substantially higher than the C. Ex. 3 fiber, which has a clean water flux of about 8 L/(h·m²·bar), and which was taught by prior art application publication '848.

Measurement of Molecular Weight Cut-Off

Prior to the measurement of the molecular weight cut-off (MWCO), all membrane modules were wetted with a mixture of 50 wt % water and 50 wt % ethanol. Next, clean water was permeated through the hollow fiber membranes for 15 minutes to remove all residual ethanol from the fibers. The measurement was started directly after the pretreatment.

Figure 5:
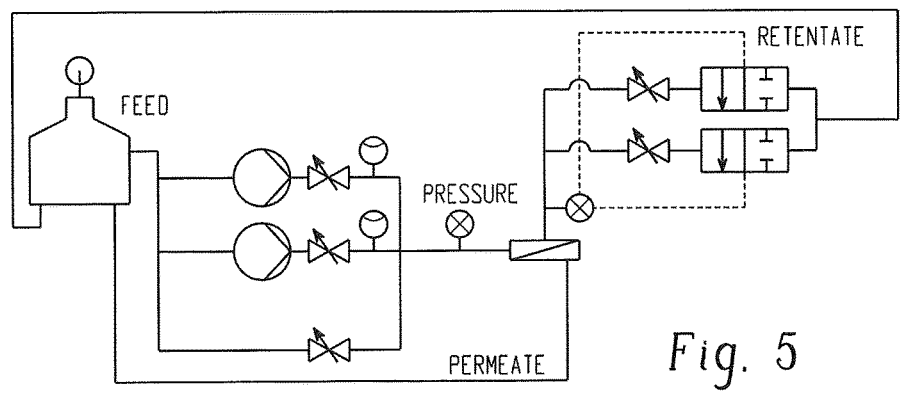
FIG. 5 depicts a diagram of a hollow fiber filtration system for measuring clean water flux and molecular weight cut-off.

FIG. 5 shows a schematic drawing of the MWCO measurement apparatus. Both ends of the hollow fiber filtration modules shown in FIG. 5 were cut and the feed solution was pumped through the inside of the hollow fibers and the retentate recirculated to the feed tank. The permeate solution is circulated across the outside of the fibers via the T-connectors and recycled to a separate feed tank. The cross flow velocity was controlled via the pump and the feed, retentate, and pressure are recorded. The permeate pressure was at ambient pressure. A valve at the retentate side can optionally be used to control the retentate pressure.

A turbulent flow inside the hollow fiber is desirable in order to prevent concentration polarization during the experiment. To provide turbulent flow, the cross flow velocity is set to target a Reynolds number of about 3000. The Reynolds number is defined according to Equation 1, whereas "$\eta$" is defined as the dynamic viscosity of the fluid, "$\rho$" is defined as the density of the fluid, "v" defined as the fluid velocity and "d" defined as the inner fiber diameter.

$$Re = \frac{\rho * v * d}{\eta} \quad \text{(Eq. 1)}$$

As a feed solution, a mixture of four different dextrans, which differ in molecular weight (1 kDa, 4 kDa, 8 kDa and 40 kDa), was used. The concentration in the feed solution was 0.5 g/L for each dextran. The molecular weight cut off is defined as that molecular weight of a species which is retained up to 90 percent by the membrane. The retention is calculated by comparing the gel permeation chromatography of the initial solution of dextrans to that measured on permeate and retentate solutions after reaching equilibrium.

Three filtration modules of each of Comparative Example 3 and Examples 18-20 were tested, and the results are summarized in Table 12. For the three PES modules of Comparative Example 3, it was possible to run the MWCO experiment under conditions of a Reynolds number (Re) of 3000. However, no MWCO was determined for two modules (Retention was always below 90 percent for the given feed.) and for the third module the MWCO was not stable over time.

In contrast to the PES/PVP hollow fibers of Comparative Example 3, the PPE copolymer hollow fibers of Examples 18-20 appeared to be defect-free under the same conditions of high Re (3,000-3,600) and high trans-membrane pressure (TMP, 1.9-3.5 bar) and yielded stable MWCO values of 6-15 kDa. Thus the membranes of Examples 18-20 provide an improved combination of higher CWF and stable low MWCO over the membrane produced from PES and PVP. In addition, the membranes of Examples 18-20 provided improved mechanical integrity. The fact that this performance can be achieved from membranes formed from inherently hydrophobic PPE resin in the absence of pore-forming additives (hydrophilic polymer), using only a simple wetting process based on aqueous ethanol, is surprising.

Stable readings were readily obtained for the additional examples: since the MWCO values at either extreme of MPP co-monomer content were essentially the same we conclude that there is no significant effect of this parameter on the ability to form well-controlled pore size distributions from the PPE during hollow fiber spinning.

TABLE 12

Molecular Weight Cut-off Measurements

| Hollow Fiber | Polymer | MWCO (kDa) | | | |
|---|---|---|---|---|---|
| | | 60 min | 75 min | 120 min | 180 min |
| CE3 | CE2 (PES/PVP) | Re = 3,000; flow = 100 L/h; TMP = 2.1 bar | | | |
| | | 10.1 | — | 44.3 | 59.3 |
| | | 90 Percent retention was not reached. | | | |
| | | 90 Percent retention was not reached. | | | |
| E18 | E12 (50/50 MPP-DMP) | Re = 3,000; Flow = 140 L/h; TMP = 2.1 bar | | | |
| | | 8.3 | 7.3 | 6.3 | — |
| | | 5.2 | 6.6 | 5.3 | — |
| | | 6.4 | 5.2 | 5.2 | — |
| | | Average = 5.6 | | | |
| E19 | E11 (20/80 MPP-DMP) | Re = 3,600; Flow = 140 L/h; TMP = 1.9 bar | | | |
| | | 61.7 | 54.5 | 51.4 | — |
| | | 15.9 | 14.6 | 13.6 | — |
| | | 12.8 | 13.6 | 13.4 | — |
| | | Average = 13.5 | | | |
| E20 | E13 (80/20 MPP-DMP) | Re = 3,250; Flow = 150 L/h; TMP = 3.5 bar | | | |
| | | 16.3 | — | 16.1 | 15.6 |
| | | 14.0 | — | 13.5 | 17.5 |
| | | 17.7 | — | 19.5 | 13.2 |
| | | Average = 15.4 | | | |

SEM Comparison of Flat Sheet and Hollow Fiber Morphology

Figure 6:
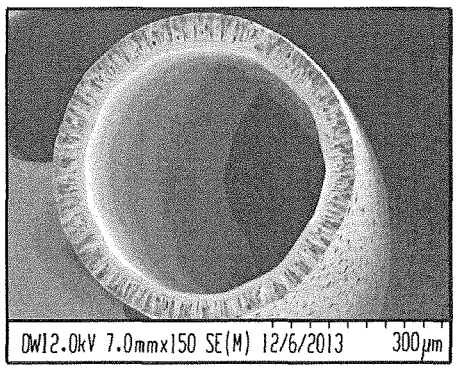
FIG. 6 depicts SEM images of the hollow fiber membranes of Comparative Example 3 and Example 18.
Figure 6:
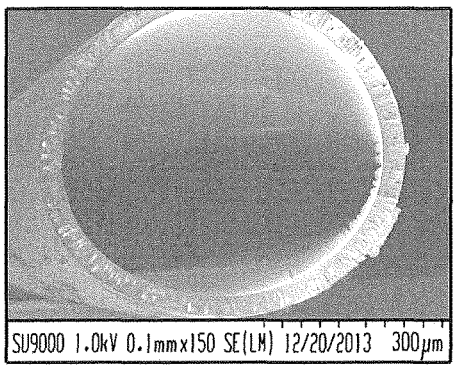
Figure 6:
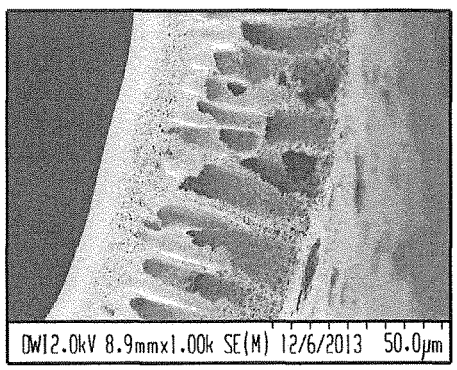
Figure 6:
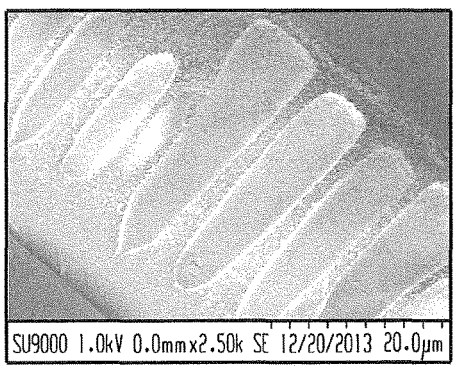
Figure 6:
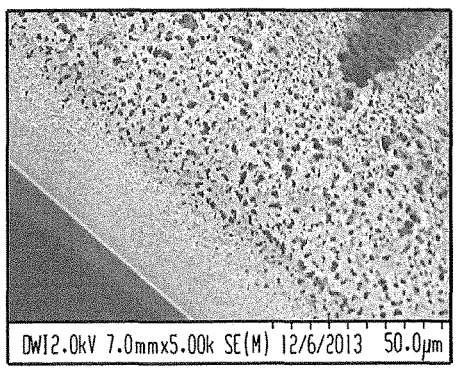
Figure 6:
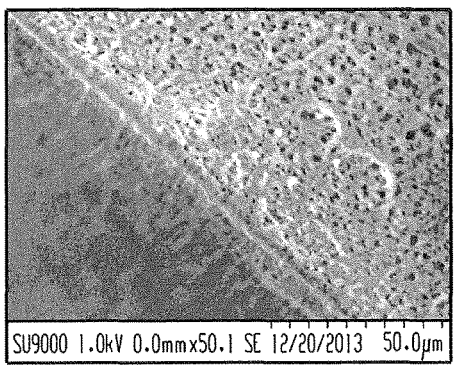

The hollow fibers of Comparative Example 3 and Example 18 were analyzed by SEM, the results of which are shown in FIG. 6. The hollow fibers of Comparative Example 3, prepared from PES and PVP, show a strongly asymmetric cross-sectional morphology, and similar to those obtained for flat membrane castings of the same dope composition (Comparative Example 2 depicted in FIG. 2). The dense selective layer appears to be thin for the PES/PVP comparative example in both the flat and the hollow fiber geometry. In comparison, the morphology of the hollow fiber of Example 18 shows a dense, spongy morphology that persists across the hollow fiber cross-section, which is also consistent with the appearance of the flat membranes produced from the same dope composition (Example 17 depicted in FIG. 2). Thus the poly(phenylene ether) co-polymers disclosed herein provide membrane-forming characteristics that are superior to those of PES/PVP polymers in both flat or hollow fiber geometries.

The use of the terms "a" and "an" and "the" and similar referents in the context of describing the invention (especially in the context of the following claims) is to be construed to cover both the singular and the plural, unless otherwise indicated herein or clearly contradicted by context. "Or" means "and/or." The endpoints of all ranges directed to the same component or property are inclusive and independently combinable. Disclosure of a narrower range or more specific group in addition to a broader range is not a disclaimer of the broader range or larger group. All ranges disclosed herein are inclusive of the endpoints, and the endpoints are independently combinable with each other. The terms "first" and "second" and the like, as used herein do not denote any order, quantity, or importance, but are only used to distinguish one element from another. The term "comprises" as used herein is understood to encompass embodiments consisting essentially of, or consisting of, the named elements.

Unless defined otherwise, technical and scientific terms used herein have the same meaning as is commonly understood by one of skill in the art to which this invention belongs. A "combination" is inclusive of blends, mixtures, alloys, reaction products, and the like.

As used herein, the term "hydrocarbyl" refers broadly to a moiety having an open valence, comprising carbon and hydrogen, optionally with 1 to 3 heteroatoms, for example, oxygen, nitrogen, halogen, silicon, sulfur, or a combination thereof. Unless indicated otherwise, the hydrocarbyl group can be unsubstituted or substituted, provided that the substitution does not significantly adversely affect synthesis, stability, or use of the compound. The term "substituted" as used herein means that at least one hydrogen on a hydrocarbyl group is replaced with another group (substituent) that contains a heteroatom selected from nitrogen, oxygen, sulfur, halogen, silicon, or a combination thereof, provided that the normal valence of any atom is not exceeded. For example, when the substituent is oxo (i.e. "=O"), then two hydrogens on a designated atom are replaced by the oxo group. Combinations of substituents and/or variables are permissible provided that the substitutions do not significantly adversely affect the synthesis, stability or use of the compound.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A porous asymmetric membrane, comprising a poly (phenylene ether) copolymer comprising repeat units derived from 2,6-dimethylphenol and repeat units derived from 2-methyl-6-phenylphenol, and having an intrinsic viscosity of 0.7 to 1.5 deciliters per gram, measured in chloroform at 25° C. and a weight average molecular weight of 100,000 to 500,000 daltons, measured by gel permeation chromatography against polystyrene standards; and an amphiphilic copolymer comprising a hydrophobic block and a hydrophilic block or graft.

2. The porous asymmetric membrane of claim 1, wherein the poly(phenylene ether) copolymer comprising:
   80 to 20 mole percent repeat units derived from 2,6-dimethylphenol; and
   20 to 80 mole percent repeat units derived from 2-methyl-6-phenol.

3. The porous asymmetric membrane of claim 1, wherein the amphiphilic copolymer comprises a block copolymer of poly(ethylene oxide) and poly(propylene oxide), polystyrene-graft-poly(ethylene glycol), or a combination thereof.

4. The porous asymmetric membrane of claim 1, wherein the hydrophobic block comprises polystyrene and the hydrophilic block or graft comprises poly(N,N-dimethylacrylamide) or poly(4-vinylpyridine).

5. The porous asymmetric membrane of claim 1, having a contact angle of 40 to 80 degrees.

6. A method of forming a porous asymmetric membrane, the method comprising:
   dissolving a poly(phenylene ether) copolymer comprising repeat units derived from 2,6-dimethylphenol and repeat units derived from 2-methyl-6-phenylphenol, and having an intrinsic viscosity of 0.7 to 1.5 deciliters per gram, measured in chloroform at 25° C. and a weight average molecular weight of 100,000 to 500,000 daltons, measured by gel permeation chromatography against polystyrene standards; and an amphiphilic copolymer comprising a hydrophobic block and a hydrophilic block or graft in a water-miscible polar aprotic solvent to form a porous asymmetric membrane-forming composition; and
   phase-inverting the porous asymmetric membrane forming-composition in a first non-solvent composition to form the porous asymmetric membrane.

7. The method of claim 6, further comprising washing the porous asymmetric membrane in a second non-solvent composition.

8. The method of claim 6, further comprising drying the porous asymmetric membrane.

9. The method of claim 6, wherein the first non-solvent composition comprises 10 to 100 weight percent water and 0 to 90 weight percent N-methyl-2-pyrrolidone, based on the total weight of the first non-solvent composition.

10. A method of making a hollow fiber by coextrusion through a spinneret comprising an annulus and a bore, wherein the method comprises coextruding:
    a membrane-forming composition comprising a hydrophobic polymer comprising a poly(phenylene ether) or poly(phenylene ether) copolymer comprising repeat units derived from 2,6-dimethylphenol and percent repeat units derived from 2-methyl-6-phenylphenol, and having an intrinsic viscosity of 0.7 to 1.5 deciliters per gram, measured in chloroform at 25° C. and a weight average molecular weight of 100,000 to 300,000 daltons, measured by gel permeation chromatography against polystyrene standards; and an amphiphilic copolymer comprising a hydrophobic block and a hydrophilic block or graft dissolved in a water-miscible polar aprotic solvent through the annulus, and
    a first non-solvent composition comprising water, a water-miscible polar aprotic solvent, or a combination comprising at least one of the foregoing, in the first non-solvent composition, through the bore,
    into a second non-solvent composition comprising water, a water-miscible polar aprotic solvent, or a combination comprising at least one of the foregoing, to form the hollow fiber.

11. The method of claim 10, further comprising washing the hollow fiber in a third non-solvent composition.

12. The method of claim 10, further comprising drying the hollow fiber.

13. A separation module comprising the porous asymmetric membrane of claim 1.

14. A hollow fiber made by the method of claim 10.

15. A separation module comprising the hollow fiber of claim 14.

16. The porous asymmetric membrane of claim 1, wherein the poly(phenylene ether) copolymer has a solubility in a water-miscible polar aprotic solvent of greater than 100 grams per kilogram at 25° C.

17. The porous asymmetric membrane of claim 1, wherein the poly(phenylene ether) copolymer has a solubility in a water-miscible polar aprotic solvent selected from the group consisting of N-methyl-2-pyrrolidone, N,N-dimethylformamide, and N,N-dimethylacetamide, of 100 to 400 grams per kilogram at 25° C.

18. The porous asymmetric membrane of claim 1, wherein the hydrophobic block of the amphiphilic block copolymer comprises an ethylenically unsaturated monomer selected from methoxy-capped poly(ethylene oxide) methacrylate, 4-vinylpyridine, N-vinylpyrrolidone, N,N-dimethylacrylamide, 4-acryloylmorpholine, or a combination comprising at least one of the foregoing.

19. The porous asymmetric membrane of claim 1, wherein the amphiphilic copolymer comprises a block copolymer of poly(ethylene oxide) and poly(propylene oxide).

* * * * *